US012655132B2

(12) United States Patent
Xue et al.

(10) Patent No.: US 12,655,132 B2
(45) Date of Patent: Jun. 16, 2026

(54) CRYSTAL FORMS OF A PYRIDAZINONE TRPC INHIBITOR

(71) Applicant: GFB (ABC), LLC, Foxboro, MA (US)

(72) Inventors: Wenfeng Xue, Suzhou (CN); Yuejun Gao, Suzhou (CN)

(73) Assignee: GFB (ABC), LLC, Foxboro (MA)

( * ) Notice: Subject to any disclaimer, the term of this patent is extended or adjusted under 35 U.S.C. 154(b) by 1062 days.

(21) Appl. No.: 17/603,249

(22) PCT Filed: Apr. 10, 2020

(86) PCT No.: PCT/US2020/027689

§ 371 (c)(1),
(2) Date: Oct. 12, 2021

(87) PCT Pub. No.: WO2020/210639

PCT Pub. Date: Oct. 15, 2020

(65) Prior Publication Data

US 2022/0177455 A1 Jun. 9, 2022

(30) Foreign Application Priority Data

Apr. 10, 2019 (WO) ................ PCT/CN2019/081985

(51) Int. Cl.
*C07D 403/14* (2006.01)

(52) U.S. Cl.
CPC ........ *C07D 403/14* (2013.01); *C07B 2200/13* (2013.01)

(58) Field of Classification Search
CPC .................................................... C07D 403/14
See application file for complete search history.

(56) References Cited

U.S. PATENT DOCUMENTS 6,946,120 B2 * 9/2005 Wai-Chiu So ....... A61K 9/0014 514/940

FOREIGN PATENT DOCUMENTS

| | | | |
|---|---|---|---|
| WO | WO-2019/055966 | A2 | 3/2019 |
| WO | WO-2020/061162 | A1 | 3/2020 |
| WO | WO-2020/206623 | A1 | 10/2020 |
| WO | WO-2020/210639 | A1 | 10/2020 |
| WO | WO-2022/001767 | A1 | 1/2022 |

OTHER PUBLICATIONS

Kazuhide Ashizawa et al., "Polymorphism and Crystallization of the Pharmaceutical Drugs," Maruzen Planet Co., Ltd., Sep. 20, 2002, pp. 305-317.
International Preliminary Report on Patentability for International Application No. PCT/US2020/027689 issued Sep. 28, 2021.
International Search Report and Written Opinion for International Application No. PCT/CN2019/081985 mailed Jan. 15, 2020.
International Search Report and Written Opinion for International Application No. PCT/US2020/027689 mailed Jun. 15, 2020.

* cited by examiner

*Primary Examiner* — John S Kenyon
(74) *Attorney, Agent, or Firm* — Honigman LLP; Andrew S. Chipouras; Jonathan P. O'Brien

(57) ABSTRACT

Disclosed are crystalline forms of Compound 100. In some embodiments, a crystalline form of Compound 100 has characteristic peaks in the XRPD pattern as shown in any one of FIGS. 1A, 2A, 3A, 4A, 5A, and 6A.

34 Claims, 7 Drawing Sheets

CRYSTAL FORMS OF A PYRIDAZINONE TRPC INHIBITOR

RELATED APPLICATIONS

This application is a National Stage Entry of International Application No. PCT/US20/27689, filed Apr. 10, 2020; which claims the benefit of priority to International Application No. PCT/CN19/81985, filed Apr. 10, 2019.

FIELD OF THE INVENTION

The present invention relates to crystalline polymorphs of Compound 100, pharmaceutical compositions comprising the same, and methods of using the same to prepare pharmaceutical compositions.

BACKGROUND

Proteinuria is a condition in which an excessive amount of protein in the blood leaks into the urine. Proteinuria can progress from a loss of 30 mg of protein in the urine over a 24-hour period (called microalbuminuria) to >300 mg/day (called macroalbuminuria), before reaching levels of 3.5 grams of protein or more over a 24-hour period, or 25 times the normal amount. Proteinuria occurs when there is a malfunction in the kidney's glomeruli, causing fluid to accumulate in the body (edema). Prolonged protein leakage has been shown to result in kidney failure. Nephrotic Syndrome (NS) disease accounts for approximately 12% of prevalent end stage renal disease cases at an annual cost in the United States of more than $3 billion. Approximately 5 out of every 100,000 children are diagnosed with NS every year and 15 out of every 100,000 children are living with it today. For patients who respond positively to treatment, the relapse frequency is extremely high. Ninety % of children with Nephrotic Syndrome will respond to treatment, however, an estimated 75% will relapse. There is a need for more effective methods of treating, or reducing risk of developing, kidney disease, e.g., proteinuria.

Mammalian TRP channel proteins form six-transmembrane cation-permeable channels that may be grouped into six subfamilies on the basis of amino acid sequence homology (TRPC, TRPV, TRPM, TRPA, TRPP, and TRPML). Recent studies of TRP channels indicate that they are involved in numerous fundamental cell functions and are considered to play an important role in the pathophysiology of many diseases. Many TRPs are expressed in kidney along different parts of the nephron and growing evidence suggest that these channels are involved in hereditary, as well as acquired kidney disorders. TRPC6, TRPM6, and TRPP2 have been implicated in hereditary focal segmental glomerulosclerosis (FSGS), hypomagnesemia with secondary hypocalcemia (HSH), and polycystic kidney disease (PKD), respectively. TRPC5 has also been implicated in FSGS and diabetic nephropathy. (J Clin Invest. 2013 Dec. 2; 123(12): 5298-5309. 10.1172/JCI71165; Zhou et al., Science 358, 1332-1336 (2017)

TRPC5 has also been reported to contribute to the mechanisms underlying regulation of innate fear responses. (J Neurosci. 2014 Mar. 5; 34(10): 3653-3667).

Hence, there is a need for additional inhibitors of TRPC5.

SUMMARY

In some aspects, the present invention is directed to a crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one selected from:

form A, which is an anhydrate and is characterized by X-ray powder diffraction peaks at 2Θ angles of 4.43±0.2°, 11.69±0.2°, 17.75±0.2° and 27.58±0.2°;

form H, which is an anhydrate and is characterized by X-ray powder diffraction peaks at 2Θ angles of 13.79±0.2°, 23.61±0.2°, and 27.10±0.2°;

form E, which is a hydrate and is characterized by X-ray powder diffraction peaks at 2Θ angles of 11.71±0.2°, 15.24±0.2°, 24.79±0.2°, and 26.15±0.2°; or form G, which is a hydrate and is characterized by X-ray powder diffraction peaks at 2Θ angles of 15.34±0.2°, 24.58±0.2°, and 25.86±0.2°.

In some aspects, the present invention is directed to a crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one is additionally selected from:

form B, which is an anhydrate and is characterized by X-ray powder diffraction peaks at 2Θ angles of 4.40±0.2°, 17.48±0.2°, 17.72±0.2° and 27.49±0.2°; or form C, which is a hydrate and is characterized by X-ray powder diffraction peaks at 2Θ angles of 4.42±0.2°, 8.83±0.2°, 13.27±0.2°, and 17.72±0.2°.

In some aspects, the present invention is directed to a pharmaceutical composition, comprising crystalline form A.

In some aspects, the present invention is directed to a pharmaceutical composition, comprising crystalline form H.

In some aspects, the present invention is directed to a pharmaceutical composition, comprising crystalline form E.

In some aspects, the present invention is directed to a pharmaceutical composition, comprising crystalline form G.

In some aspects, the present invention is directed to a pharmaceutical composition, comprising crystalline form B.

In some aspects, the present invention is directed to a pharmaceutical composition, comprising crystalline form C.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising combining a sample of crystalline form A, and a pharmaceutically acceptable carrier.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of:

a. dissolving crystalline form A in a solvent to form a solution; and b. preparing the pharmaceutical composition from the solution.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising combining a sample of crystalline form H, and a pharmaceutically acceptable carrier.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of a. dissolving crystalline form H in a solvent to form a solution; and b. preparing the pharmaceutical composition from the solution.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising combining a sample of crystalline form E, and a pharmaceutically acceptable carrier.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of a. dissolving crystalline form E in a solvent to form a solution; and
b. preparing the pharmaceutical composition from the solution.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising combining a sample of crystalline form G, and a pharmaceutically acceptable carrier.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of a. dissolving crystalline form G in a solvent to form a solution; and
b. preparing the pharmaceutical composition from the solution.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising combining a sample of crystalline form B, and a pharmaceutically acceptable carrier.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of a. dissolving crystalline form B in a solvent to form a solution; and
b. preparing the pharmaceutical composition from the solution.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising combining a sample of crystalline form C, and a pharmaceutically acceptable carrier.

In some aspects, the present invention is directed to a method of preparing a pharmaceutical composition of 4-chloro-5-(4-(4-fluoro-2-(trifluoromethyl)phenoxy)-5,8-dihydropyrido[3,4-d]pyrimidin-7(6H)-yl)pyridazin-3(2H)-one, comprising the steps of a. dissolving crystalline form C in a solvent to form a solution; and b. preparing the pharmaceutical composition from the solution.

In some embodiments, the present invention is directed to a method of inhibiting one or more of TRPC1, TRPC4, and TRPC5 ion channels, or ion channels comprising a tetrameric combination of any of TRPC1, TRPC4, and TRPC5, in a subject in need of thereof, comprising administering to the subject an effective amount of a pharmaceutical composition, comprising a crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one. In some aspects of these embodiment, the ion channel is a heterotetrameric form, comprising a combination of one or more TRPC1 ion channels with one or more TRPC4 and/or TRPC5 ion channels. In some aspects of these embodiments, the ion channel is a heterotetrameric form, comprising one or more TRPC4 ion channels and one or more TRPC5 ion channels.

In some aspects, the present invention is directed to a method of treating a kidney disease or a nephropathy associated with a condition or disease comprising administering to a subject in need thereof a therapeutically effective amount a pharmaceutical composition comprising a crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one.

In some aspects, the present invention is directed to a method of preparing the crystalline form A, comprising the steps of:

a. dissolving an amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in an amount of a 2:1 (v/v) ratio of DMSO:ethanol at room temperature to form a supersaturated solution;
b. adding to the solution in step a. an amount of a 1:1 (v/v) ratio of ethanol:$H_2O$ sufficient to precipitate the 4-chloro-5-(4-(4-fluoro-2-(trifluoromethyl)phenoxy)-5,8-dihydropyrido[3,4-d]pyrimidin-7(6H)-yl)pyridazin-3 (2H)-one; and
c. isolating the precipitated material from step b. to produce the crystalline form A.

In some aspects, the present invention is directed to a method of preparing the crystalline form A, comprising the steps of:

a. dissolving an amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in an amount of a 2:1 (v/v) ratio of DMSO:ethanol at room temperature to form a supersaturated solution;
b. adding to the solution in step a. an amount of a 1:1 (v/v) ratio of ethanol:$H_2O$ and crystal form A seeds to precipitate the 4-chloro-5-(4-(4-fluoro-2-(trifluoromethyl)phenoxy)-5,8-dihydropyrido[3,4-d]pyrimidin-7(6H)-yl)pyridazin-3 (2H)-one; and
c. isolating the precipitated material from step b. to produce the crystalline form A.

In some aspects, the present invention is directed to a method of preparing the crystalline form H comprising the steps of:

a. suspending 4-chloro-5-(4-(4-fluoro-2-(trifluoromethyl)phenoxy)-5,8-dihydropyrido[3,4-d]pyrimidin-7(6H)-yl)pyridazin-3(2H)-one in a 1:1 (v/v) ratio of isopropyl alcohol:isopropyl acetate;
b. heating the suspension of step a. to a temperature of between 45°-55° C. for at least 24 hours with stirring; and
c. isolating the insoluble material from step b. to produce the crystalline form H.

In some aspects, the present invention is directed to a method of preparing the crystalline form H comprising the steps of:

a. dissolving 4-chloro-5-(4-(4-fluoro-2-(trifluoromethyl)phenoxy)-5,8-dihydropyrido[3,4-d]pyrimidin-7(6H)-yl)pyridazin-3(2H)-one in a 2:1 (v/v) ratio of DMSO:isopropyl alcohol at a temperature of between 45°-55° C.;
b. filtering the solution from step a. through a 0.45 micron PTFE membrane;

c. adding to the filtrate from step b. (i) an amount of isopropyl alcohol that is 30-50% of the amount of isopropyl alcohol used in step a.; and (ii) crystalline form H and stirring at a temperature of between 45°-55° C. for at least 5 minutes;

d. adding to the solution from step c. a 1:1 (v/v) ratio of isopropyl alcohol:$H_2O$ over a period of at least 4 hours with stirring while maintaining a temperature of between 45°-55° C. to produce a suspension of 4-chloro-5-(4-(4-fluoro-2-(trifluoromethyl)phenoxy)-5,8-dihydropyrido[3,4-d]pyrimidin-7(6H)-yl)pyridazin-3(2H)-one, wherein the amount of isopropyl alcohol added in steps c. and d. is about the amount of isopropyl alcohol added in step a.;

e. maintaining the suspension from step d. at a temperature of between 45°-55° C. without stirring for at least 2 hours; and f. isolating the precipitated material from step e. to produce the crystalline form H.

In some aspects, the present invention is directed to a method of preparing the crystalline form H comprising the steps of:

a. dissolving 4-chloro-5-(4-(4-fluoro-2-(trifluoromethyl)phenoxy)-5,8-dihydropyrido[3,4-d]pyrimidin-7(6H)-yl)pyridazin-3(2H)-one in DMSO at a temperature of between 65°-75° C.;

b. filtering the solution from step a. through a 0.45 micron PTFE membrane;

c. adding to the filtrate from step b. (i) an amount of a 1:1 (v/v) ratio of isopropyl alcohol:$H_2O$ that is about 10% of the volume of DMSO used in step A; and (ii) crystalline form H;

d. adding to the filtrate from step c. an additional amount of a 1:1 (v/v) ratio of isopropyl alcohol:$H_2O$ over a period of at least 5 hours with stirring while maintaining a temperature of between 65°-75° C., to produce a suspension of 4-chloro-5-(4-(4-fluoro-2-(trifluoromethyl)phenoxy)-5,8-dihydropyrido[3,4-d]pyrimidin-7(6H)-yl)pyridazin-3(2H)-one, wherein the total amount of isopropyl alcohol added in steps c. and d. is about half the volume of DMSO used in step a.;

e. cooling the suspension of step d. to room temperature with stirring for at least 2 hours;

f. maintaining the suspension of step e. at room temperature without stirring for at least an additional 45 minutes; and g. isolating the precipitated material from step f. to produce the crystalline form H.

In some aspects, the present invention is directed to a method of forming crystal form E comprising the steps of:

a. suspending 4-chloro-5-(4-(4-fluoro-2-(trifluoromethyl)phenoxy)-5,8-dihydropyrido[3,4-d]pyrimidin-7(6H)-yl)pyridazin-3(2H)-one in DMF/$H_2O$ (1:9, v/v) at room temperature to form a slurry; and b. vacuum drying the suspension.

In some aspects, the present invention is directed to a method of forming crystal form G comprising the steps of:

a. suspending 4-chloro-5-(4-(4-fluoro-2-(trifluoromethyl)phenoxy)-5,8-dihydropyrido[3,4-d]pyrimidin-7(6H)-yl)pyridazin-3(2H)-one in a solvent having a $a_w$ of greater than or equal to 0.8 at room temperature to form a slurry; and b. vacuum drying the suspension.

BRIEF DESCRIPTION OF THE DRAWINGS

The drawings are provided for illustration, not limitation.

DETAILED DESCRIPTION

The present invention features crystalline polymorphs of Compound 100, (100)

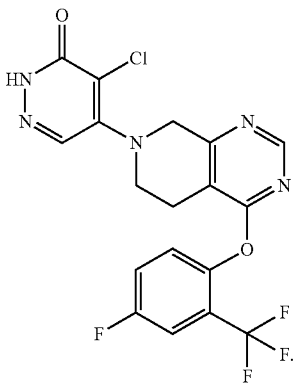

Compound 100 is an inhibitor of TRPC1, TRPC4, and TRPC5, described in WO 20/061162; US 2020/0102301; U.S. patent application Ser. No. 16/575,161, filed Sep. 18, 2019; 62/732,728, filed Sep. 18, 2018; and 62/780,553, filed Dec. 17, 201; all of which are incorporated herein by reference.

A crystalline form of Compound 100 can be used to modulate/improve the physicochemical properties of the compound, including but not limited to solid state properties (e.g., crystallinity, hygroscopicity, melting point, or hydration), pharmaceutical properties (e.g., solubility/dissolution rate, stability, or compatibility), as well as crystallization characteristics (e.g., purity, yield, or morphology).

Figure 1A:
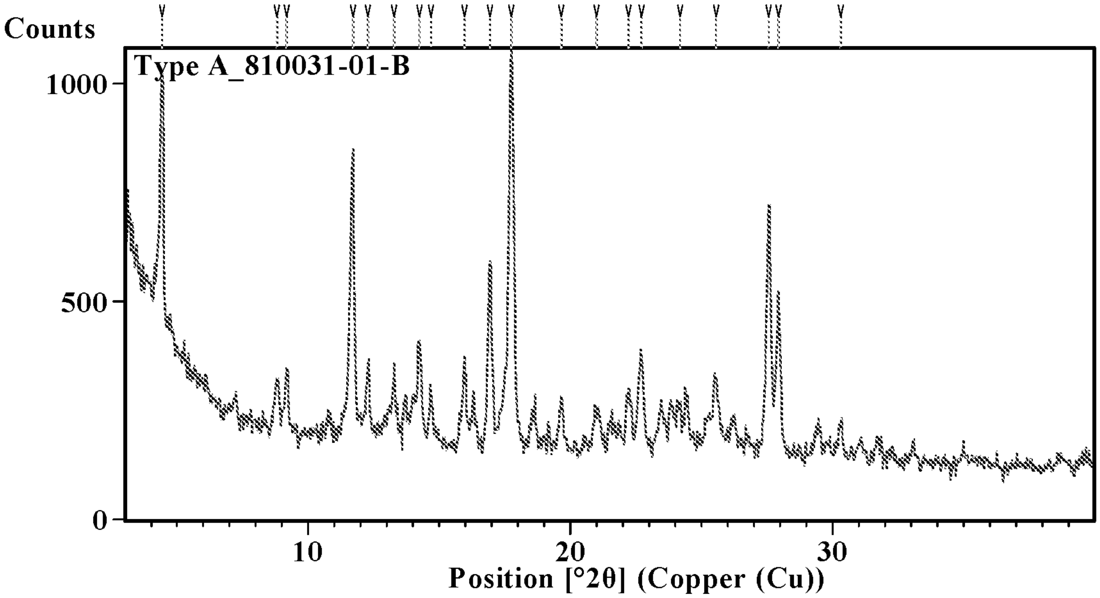
FIG. 1A shows experimental XRPD pattern of crystalline Form A of Compound 100.

In one aspect, the invention features a crystalline form A of Compound 100 which has characteristic peaks in the X-ray powder diffraction (XRPD) pattern substantially similar to FIG. 1A.

In another aspect, the invention features a crystalline form A of Compound 100 which has characteristic peaks in the X-ray powder diffraction (XRPD) pattern at values of two theta (° 2θ) as shown in Table 1.

The relative intensity, as well as the two theta value, of each peak in Tables 1, 2, 3 and 4, as well as FIGS. 1A, 2A, 3A, and 4A, may change or shift under certain conditions, although the crystalline form is the same. One of ordinary skill in the art should be able to readily determine whether a given crystalline form is the same crystalline form as described in one of FIGS. 1A, 2A, 3A, and 4A or Tables 1, 2, 3 and 4 by comparing their XRPD data. As used herein, a XRPD dataset is "substantially similar to" another XRPD dataset if one or more of the peaks in one dataset are within ±0.2° 2θ of the corresponding peaks in the other dataset.

In yet another aspect, the invention features a crystalline form A of Compound 100 which has characteristic peaks in the X-ray powder diffraction (XRPD) pattern at values of two theta (° 2θ) of 4.43±0.2°, 11.69±0.2°, 17.75±0.2° and 27.58±0.2°. In some embodiments, the indicated characteristic peaks are the highest peaks in the XRPD pattern.

In yet another aspect, the invention features a crystalline form A of Compound 100, which has characteristic peaks in the X-ray powder diffraction (XRPD) pattern at values of two theta (° 2θ) of 4.43±0.2°, 8.80±0.2°, 9.17±0.2°, 11.69±0.2°, 12.27±0.2°, 13.28±0.2°, 14.24±0.2°, 14.67±0.2°, 15.96±0.2°, 16.93±0.2°, 17.75±0.2°, 19.64±0.2°, 20.98±0.2°, 22.23±0.2°, 22.71±0.2°, 24.19±0.2°, 25.55±0.2°, 27.58±0.2°, 27.95±0.2°, and 30.32±0.2°.

In yet another aspect, the invention features a crystalline form A of Compound 100 characterized by a differential scanning calorimetry pattern with onsets at between 237±2° C. and 256° C.±2° C. In some embodiments, the invention features a crystalline form A of Compound 100 characterized by a differential scanning calorimetry pattern with onsets at 236.4±1° C., 243.5±1° C., and 256.3° C.±1° C.

Figure 2A:
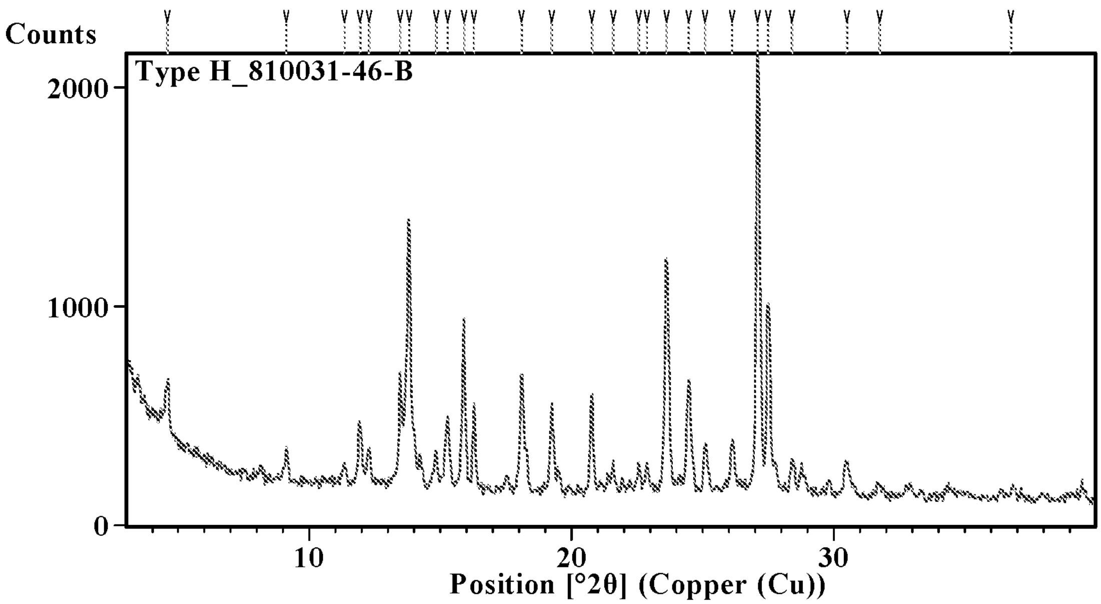
FIG. 2A shows experimental XRPD pattern of crystalline form H of Compound 100.

In yet another aspect, the invention features a crystalline form H of Compound 100 which has characteristic peaks in the X-ray powder diffraction (XRPD) pattern substantially similar to FIG. 2A.

In yet another aspect, the invention features a crystalline form H of Compound 100 which has characteristic peaks in the X-ray powder diffraction (XRPD) pattern at values of two theta (° 2θ) as shown in Table 2.

In yet another aspect, the invention features a crystalline form H of Compound 100 which has characteristic peaks in the X-ray powder diffraction (XRPD) pattern at values of two theta (° 2θ) of 13.79±0.2°, 23.61±0.2°, and 27.10±0.2°. In some embodiments, the indicated characteristic peaks are the highest peaks in the XRPD pattern.

In yet another aspect, the invention features a crystalline form H of Compound 100 which has characteristic peaks in the X-ray powder diffraction (XRPD) pattern at values of two theta (° 2θ) of 13.79±0.2°, 23.61±0.2°, 27.10±0.2°, and 27.49±0.2°. In some embodiments, the indicated characteristic peaks are the highest peaks in the XRPD pattern.

In yet another aspect, the invention features a crystalline form H of Compound 100, which has characteristic peaks in the X-ray powder diffraction (XRPD) pattern at values of two theta (° 2θ) of 4.59±0.2°, 11.92±0.2°, 12.27±0.2°, 13.47±0.2°, 13.79±0.2°, 14.82±0.2°, 15.27±0.2°, 15.89±0.2°, 16.28±0.2°, 18.08±0.2°, 19.24±0.2°, 20.77±0.2°, 23.61±0.2°, 24.47±0.2°, 25.11±0.2°, 26.13±0.2°, 27.10±0.2°, 27.49±0.2°, 28.42±0.2°, and 30.49±0.2°.

In yet another aspect, the invention features a crystalline form H of Compound 100 characterized by a differential scanning calorimetry pattern having an onset at 258°±2° C. More specifically, the invention features a crystalline form H of Compound 100 characterized by a differential scanning calorimetry pattern having onsets at 74.1° C.±1° C., 241.4° C.±1° C., and 257.0° C.±1° C.

Figure 3A:
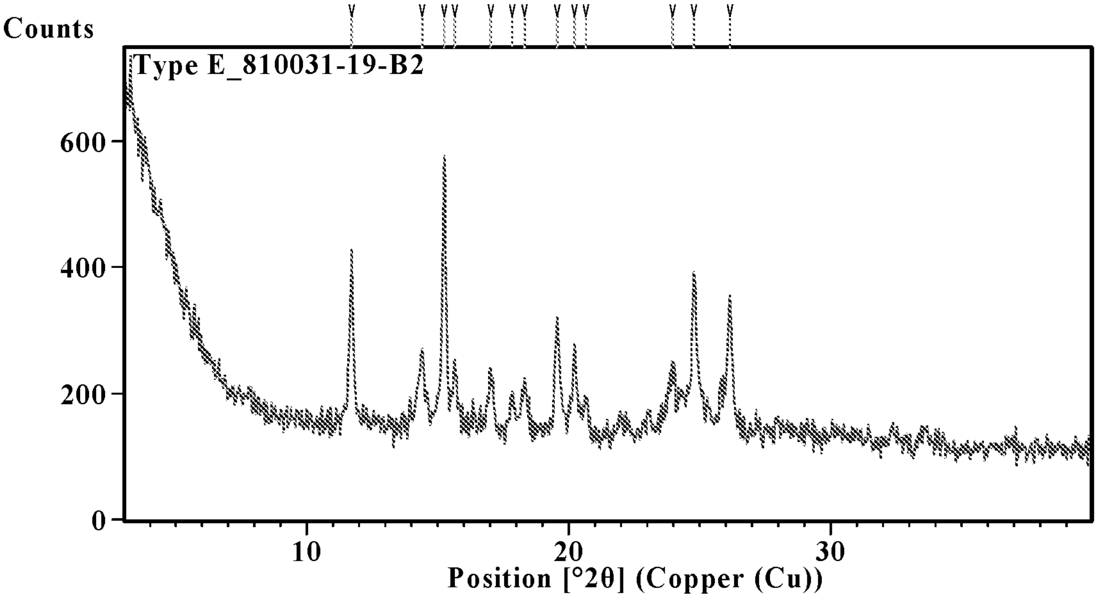
FIG. 3A shows experimental XRPD pattern of crystalline form E of Compound 100.

In yet another aspect, the invention features a crystalline form E of Compound 100 which has characteristic peaks in the X-ray powder diffraction (XRPD) pattern substantially similar to FIG. 3A.

In yet another aspect, the invention features a crystalline form E of Compound 100 which has characteristic peaks in the X-ray powder diffraction (XRPD) pattern at values of two theta (° 2θ) as shown in Table 3.

In yet another aspect, the invention features a crystalline form E of Compound 100 which has characteristic peaks in the X-ray powder diffraction (XRPD) pattern at values of two theta (° 2θ) of 11.71±0.2°, 15.24±0.2°, 24.79±0.2°, and 26.15±0.2°. In some embodiments, the indicated characteristic peaks are the highest peaks in the XRPD pattern.

In yet another aspect, the invention features a crystalline form E of Compound 100 which has characteristic peaks in the X-ray powder diffraction (XRPD) pattern at values of two theta (° 2θ) of 11.71±0.2°, 14.39±0.2°, 15.24±0.2°, 15.63±0.2°, 17.02±0.2°, 17.84±0.2°, 18.30±0.2°, 19.56±0.2°, 20.22±0.2°, 20.65±0.2°, 23.96±0.2°, 24.79±0.2°, and 26.15±0.2°.

In yet another aspect, the invention features a crystalline form E of Compound 100 characterized by a differential scanning calorimetry pattern having an onset at 78.5° C.±2° C. and 256.7° C.±2° C. In some embodiments, there is an additional onset at 257.9° C.±2° C.

Figure 4A:
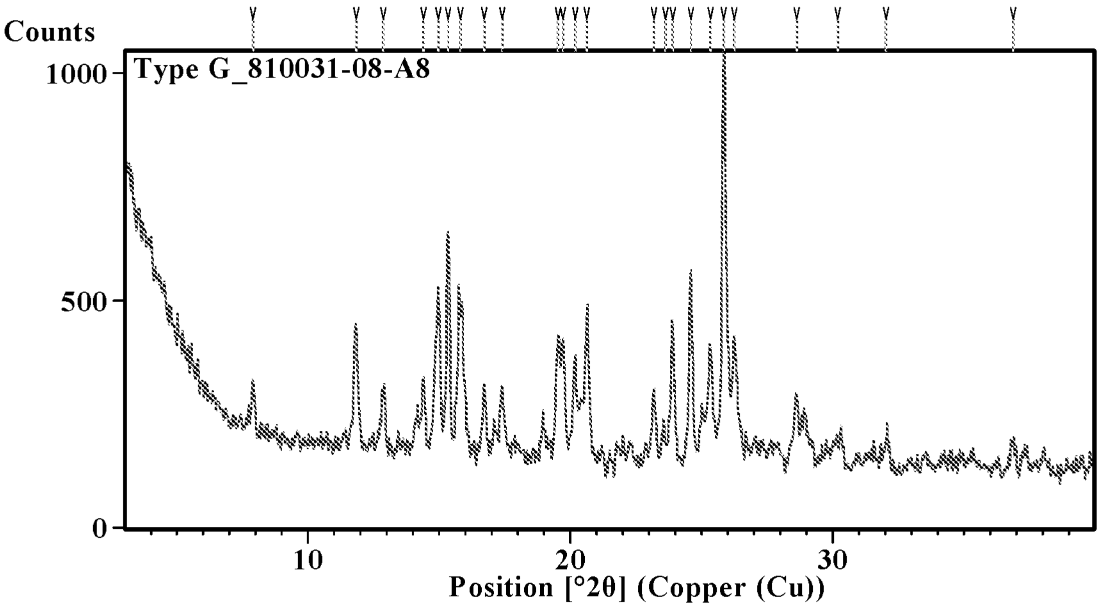
FIG. 4A shows experimental XRPD pattern of crystalline form G of Compound 100.

In yet another aspect, the invention features a crystalline form G of Compound 100 which has characteristic peaks in the X-ray powder diffraction (XRPD) pattern substantially similar to FIG. 4A.

In yet another aspect, the invention features a crystalline form G of Compound 100 which has characteristic peaks in the X-ray powder diffraction (XRPD) pattern at values of two theta (° 2θ) as shown in Table 4.

In yet another aspect, the invention features a crystalline form G of Compound 100 which has characteristic peaks in the X-ray powder diffraction (XRPD) pattern at values of two theta (° 2θ) of 15.34±0.2°, 24.58±0.2°, and 25.86±0.2°. In some embodiments, the indicated characteristic peaks are the highest peaks in the XRPD pattern.

In yet another aspect, the invention features a crystalline form G of Compound 100, which has characteristic peaks in the X-ray powder diffraction (XRPD) pattern at values of two theta (° 2θ) of 7.88±0.2°, 11.82±0.2°, 12.85±0.2°, 14.39±0.2°, 14.96±0.2°, 15.34±0.2°, 15.81±0.2°, 16.70±0.2°, 17.40±0.2°, 19.51±0.2°, 19.72±0.2°, 20.17±0.2°, 20.63±0.2°, 23.18±0.2°, 23.90±0.2°, 24.58±0.2°, 25.33±0.2°, 25.86±0.2°, 26.26±0.2°, and 28.61±0.2°.

In yet another aspect, the invention features a crystalline form G of compound 100 characterized by a differential scanning calorimetry pattern having an onset at 80.5°±2° C. C and 257.2° C.±2° C. In some embodiments, there is an additional onset at 258.3° C.±2° C.

Figure 5A:
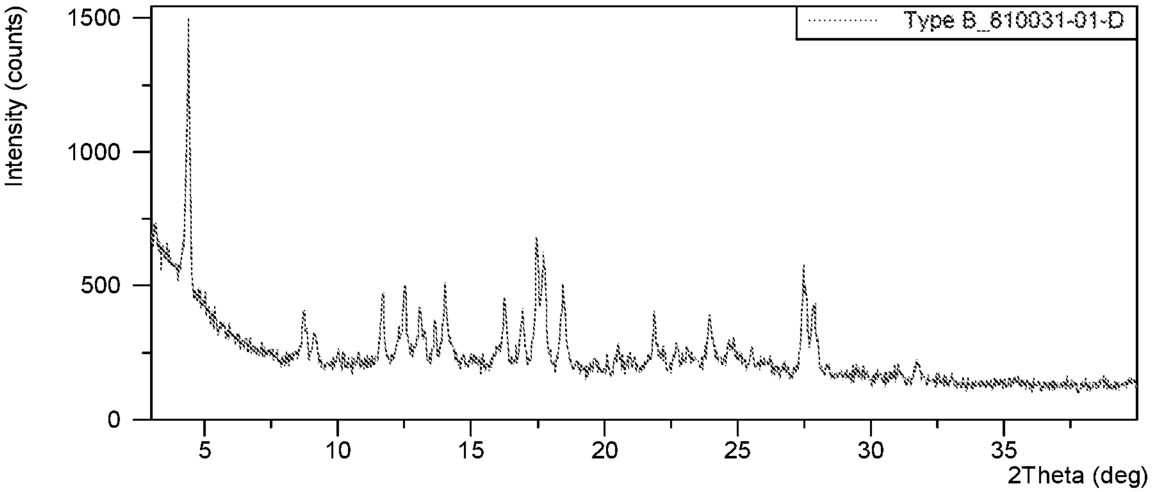
FIG. 5A shows experimental XRPD pattern of crystalline form B of Compound 100.

In yet another aspect, the invention features a crystalline form B of Compound 100 which has characteristic peaks in the X-ray powder diffraction (XRPD) pattern substantially similar to FIG. 5A.

In yet another aspect, the invention features a crystalline form B of Compound 100 which has characteristic peaks in the X-ray powder diffraction (XRPD) pattern at values of two theta (° 2θ) as shown in Table 5

In yet another aspect, the invention features a crystalline form B of Compound 100 which has characteristic peaks in the X-ray powder diffraction (XRPD) pattern at values of two theta (° 2θ) of 4.40±0.2°, 17.48±0.2°, 17.72±0.2°, 18.46±0.2°, and 27.49±0.2°. In some embodiments, the indicated characteristic peaks are the highest peaks in the XRPD pattern.

In yet another aspect, the invention features a crystalline form B of Compound 100, which has characteristic peaks in the X-ray powder diffraction (XRPD) pattern at values of two theta (° 2θ) of 4.40±0.2°, 8.74±0.2°, 9.13±0.2°, 11.67±0.2°, 12.51±0.2°, 13.10±0.2°, 13.64±0.2°, 14.03±0.2°, 16.26±0.2°, 16.93±0.2°, 17.48±0.2°, 17.72±0.2°, 18.46±0.2°, 20.51±0.2°, 21.89±0.2°, 23.97±0.2°, 24.79±0.2°, 27.49±0.2°, 27.86±0.2°, and 31.76±0.2°.

In yet another aspect, the invention features a crystalline form B of compound 100 characterized by a differential scanning calorimetry pattern having an onset at 254.5°±2° C. In some embodiments there is an additional onset at 256.3±2° C.

Figure 6A:
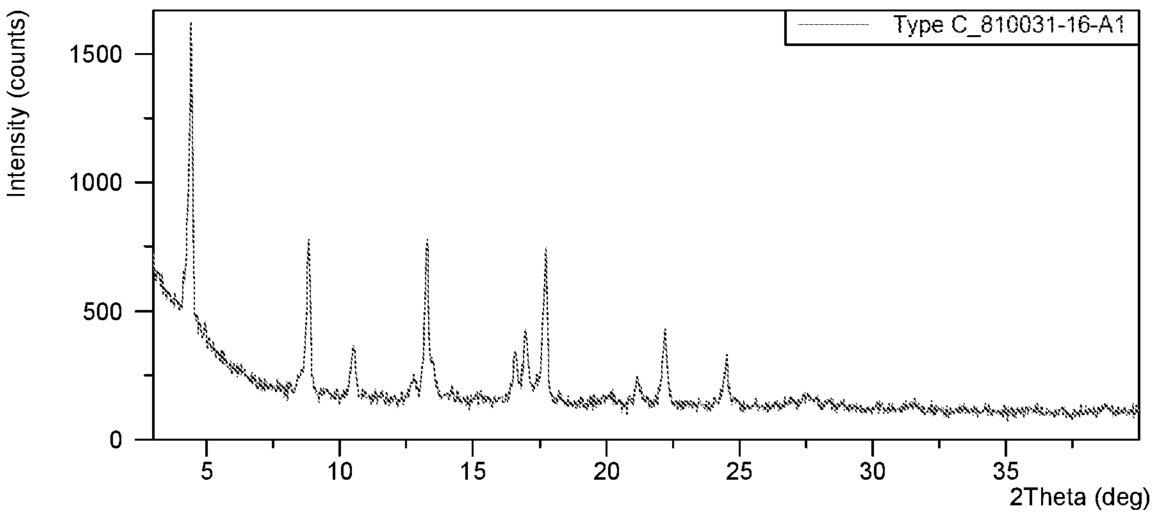
FIG. 6A shows experimental XRPD pattern of crystalline form C of Compound 100.

In yet another aspect, the invention features a crystalline form C of Compound 100 which has characteristic peaks in the X-ray powder diffraction (XRPD) pattern substantially similar to FIG. 6A.

In yet another aspect, the invention features a crystalline form C of Compound 100 which has characteristic peaks in the X-ray powder diffraction (XRPD) pattern at values of two theta (° 2θ) as shown in Table 6.

In yet another aspect, the invention features a crystalline form C of Compound 100 which has characteristic peaks in the X-ray powder diffraction (XRPD) pattern at values of two theta (° 2θ) of 4.42±0.2°, 8.83±0.2°, 13.27±0.2°, and 17.72±0.2°. In some embodiments, the indicated characteristic peaks are the highest peaks in the XRPD pattern.

In yet another aspect, the invention features a crystalline form C of Compound 100, which has characteristic peaks in the X-ray powder diffraction (XRPD) pattern at values of two theta (° 2θ) of 4.42±0.2°, 8.83±0.2°, 10.52±0.2°, 13.27±0.2°, 16.58±0.2°, 16.97±0.2°, 17.72±0.2°, 21.18±0.2°, 22.21±0.2°, and 24.49.±0.2°.

In yet another aspect, the invention features a crystalline form C of compound 100 characterized by a differential scanning calorimetry pattern having an onset at 49.6° C.±2° C., and 257.9° C.±2° C. In some embodiments, there is an additional onset at 258.9° C.±2° C.

As used herein, XRPD data can be collected using a D8 ADVANCE X-ray diffractometer (Bruker) equipped with a LynxEye detector. In XRPD analysis, samples were scanned from 3 to 40° (2θ), with a step time of 0.3 s. The tube voltage and current were 40 KV and 40 mA, respectively. XRPD peak position measurement error is typically ±0.2 degrees two-theta (° 2θ). Alternatively, XRPD data can be collected using PANalytical Empyrean and X'Pert3 X-ray powder diffractometers using the following parameters:

| Parameters | Empyrean (reflection mode) | X' Pert3 (reflection mode) | X' Pert3 (transmission mode) |
|---|---|---|---|
| X-Ray | | Cu, Kα, Kα1 (Å): 1.540598; Kα2 (Å): 1.544426 Kα2/Kα1 intensity ratio: 0.50 | |
| X-Ray tube setting | 45 kV, 40 mA | 45 kV, 40 mA | 45 kV, 40 mA |
| Divergence slit | Automatic | 1/8° | 1/2° |
| Scan mode | Continuous | Continuous | Continuous |
| Scan range (°2Theta) | 3~40 | 3~40 | 3~40 |
| Step size (°2Theta) | 0.0167 | 0.0263 | 0.0131 |
| Scan step time (s) | 33.02 | 46.67 | 14.38 |
| Test time (min) | ~10 min | ~5 min | ~5 min |

As used herein, differential scanning calorimetry (DSC) data can be collected using a Discovery DSC 250 (TA Instruments, US). A weighted sample is placed into a DSC pinhole pan, and the weight is accurately recorded. The sample is heated at 10° C./min to the final temperature. As used herein, a DSC dataset is "substantially similar to" another DSC dataset if one or more of the features in one dataset are within ±3° C. of the corresponding features in the other dataset.

As used herein, thermogravimetric analysis (TGA) data can be collected using a Discovery TGA 55 (TA Instruments, US). The sample can be placed in an open tarred aluminum pan, automatically weighed, and inserted into the TGA furnace. The sample can be heated at 10° C./min to the final temperature.

Alternatively, TGA and DSC data can be collected using a TA Q500/Q5000/5500 TGA from TA Instruments and a TA Q200/Q2000/2500 DSC from TA Instruments, respectively, using the following parameters:

| Parameters | TGA | DSC |
|---|---|---|
| Method | Ramp | Ramp |
| Sample pan | Aluminum, open | Aluminum, crimped |
| Temperature | RT-350° C. | 25-270° C. |
| Heating rate | 10° C./min | 10° C./min |
| Purge gas | $N_2$ | $N_2$ |

In another aspect, the present invention features any one of the embodiments of the crystalline forms described above, and which is substantially pure. As used herein, the term "substantially pure", when used in reference to a given crystalline form, refers to the crystalline form which is at least about 90% pure. This means that the crystalline form does not contain more than about 10% of any other form of Compound 100. More preferably, the term "substantially pure" refers to a crystalline form of Compound 100 which is at least about 95% pure. This means that the crystalline form of Compound 100 does not contain more than about 5% of any other form of Compound 100. Even more preferably, the term "substantially pure" refers to a crystalline form of Compound 100 which is at least about 97% pure. This means that the crystalline form of Compound 100 does not contain more than about 3% of any other form of Compound 100. As used herein, the term "about" is defined as being close to as understood by one of ordinary skill in the art. In one non-limiting embodiment, when used in reference to amounts or volumes of reagents or solvents, the term "about" is defined to be within 10%, preferably within 5%, more preferably within 1%, and most preferably within 0.5%.

In yet another aspect, the present invention features processes of using a crystalline form of the invention to make a composition comprising Compound 100, such as a pharmaceutical composition.

The compositions and methods of the present invention may be utilized to treat a subject in need thereof. In certain embodiments, the subject is a mammal such as a human, or a non-human mammal. When administered to subject, such as a human, the composition or the compound is preferably administered as a pharmaceutical composition comprising, for example, a compound of the invention and a pharmaceutically acceptable carrier. Pharmaceutically acceptable carriers are well known in the art and include, for example, aqueous solutions such as water or physiologically buffered saline or other solvents or vehicles such as glycols, glycerol, oils such as olive oil, or injectable organic esters. In preferred embodiments, when such pharmaceutical compositions are for human administration, particularly for invasive routes of administration (i.e., routes, such as injection or implantation, that circumvent transport or diffusion through an epithelial barrier), the aqueous solution is pyrogen-free, or substantially pyrogen-free. The excipients can be chosen, for example, to effect delayed release of an agent. The pharmaceutical composition can be in dosage unit form such as tablet, capsule (including sprinkle capsule and gelatin capsule), granule, lyophile for reconstitution, powder, solution, or syrup. In some aspects, the composition is a tablet or capsule.

A pharmaceutically acceptable carrier can contain physiologically acceptable agents that act, for example, to stabilize, increase solubility or to increase the absorption of a compound such as a compound of the invention. Such physiologically acceptable agents include, for example, carbohydrates, such as glucose, sucrose or dextrans, antioxidants, such as ascorbic acid or glutathione, chelating agents, low molecular weight proteins or other stabilizers or excipients. The choice of a pharmaceutically acceptable carrier, including a physiologically acceptable agent, depends, for example, on the route of administration of the composition.

The phrase "pharmaceutically acceptable" is employed herein to refer to those compounds, materials, compositions, and/or dosage forms which are, within the scope of sound medical judgment, suitable for use in contact with the tissues of a subject without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material. Each carrier must be "acceptable" in the sense of being compatible with the other ingredients of the formulation and not injurious to the subject. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

A pharmaceutical composition (preparation) of the present invention is preferably administered to a subject orally.

The formulations may conveniently be presented in unit dosage form and may be prepared by any methods well known in the art of pharmacy. The amount of active ingredient which can be combined with a carrier material to produce a single dosage form will vary depending upon the subject being treated, the particular mode of administration. The amount of active ingredient that can be combined with a carrier material to produce a single dosage form will generally be that amount of the compound which produces a therapeutic effect. Generally, out of one hundred percent, this amount will range from about 0.5 percent to about ninety-nine percent of active ingredient, preferably from about 0.75 percent to about 40 percent, most preferably from about 0.8 percent to about 12.5 percent.

Methods of preparing these formulations or compositions include the step of bringing into association a crystalline form of the invention, with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

To prepare solid dosage forms for oral administration (capsules (including sprinkle capsules and gelatin capsules), tablets, pills, dragees, powders, granules and the like), the active ingredient is mixed with one or more pharmaceutically acceptable carriers, such as sodium citrate or dicalcium phosphate or a solvent, and/or any of the following: (1) fillers or extenders, such as starches, lactose, sucrose, glucose, mannitol, microcrystalline cellulose, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, sodium carbonate, and cross-linked carboxymethylcellulose salts; (5) solution retarding agents, such as paraffin; (6) absorption accelerators, such as quaternary ammonium compounds; (7) wetting agents, such as, for example, cetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, stearyl fumarate sodium, and mixtures thereof; (10) complexing agents, such as, modified and unmodified cyclodextrins; (11) coloring agents; (12) glidants, such as colloidal silicon dioxide; and (12) hydrophilic polymers. In the case of capsules (including sprinkle capsules and gelatin capsules), tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The selected dosage level will depend upon a variety of factors including the activity of the particular compound or combination of compounds employed, or the ester, salt or amide thereof, the route of administration, the time of administration, the rate of excretion of the particular compound(s) being employed, the duration of the treatment, other drugs, compounds and/or materials used in combination with the particular compound(s) employed, the age, sex, weight, condition, general health and prior medical history of the subject being treated, and like factors well known in the medical arts.

A physician or veterinarian having ordinary skill in the art can readily determine and prescribe the therapeutically effective amount of the pharmaceutical composition required. For example, the physician or veterinarian could start doses of the pharmaceutical composition or compound at levels lower than that required in order to achieve the desired therapeutic effect and gradually increase the dosage until the desired effect is achieved. By "therapeutically effective amount" is meant the concentration of a compound that is sufficient to elicit the desired therapeutic effect. It is generally understood that the effective amount of the compound will vary according to the weight, sex, age, and medical history of the subject. Other factors which influence the effective amount may include, but are not limited to, the severity of the subject's condition, the disorder being treated, the stability of the compound, and, if desired, another type of therapeutic agent being administered with the compound of the invention. A larger total dose can be delivered by multiple administrations of the agent. Methods to determine efficacy and dosage are known to those skilled in the art (Isselbacher et al. (1996) Harrison's Principles of Internal Medicine 13 ed., 1814-1882, herein incorporated by reference).

In general, a suitable daily dose of an active compound used in the compositions and methods of the invention will be that amount of the compound that is the lowest dose effective to produce a therapeutic effect. Such an effective dose will generally depend upon the factors described above.

If desired, the effective daily dose of the active compound may be administered as one, two, three, four, five, six or more sub-doses administered separately at appropriate intervals throughout the day, optionally, in unit dosage forms. In certain embodiments of the present invention, the active compound may be administered two or three times daily. In preferred embodiments, the active compound will be administered once daily.

In certain embodiments, compounds of the invention may be used alone or conjointly administered with another type of therapeutic agent. As used herein, the phrase "conjoint administration" refers to any form of administration of two or more different therapeutic compounds such that the second compound is administered while the previously administered therapeutic compound is still effective in the body (e.g., the two compounds are simultaneously effective in the subject, which may include synergistic effects of the two compounds). For example, the different therapeutic compounds can be administered either in the same formulation or in a separate formulation, either concomitantly or sequentially. In certain embodiments, the different therapeutic compounds can be administered within one hour, 12 hours, 24 hours, 36 hours, 48 hours, 72 hours, or a week of one another. Thus, a subject who receives such treatment can benefit from a combined effect of different therapeutic compounds.

In certain embodiments, conjoint administration of compounds of the invention with one or more additional therapeutic agent(s) provides improved efficacy relative to each individual administration of the compound of the invention or the one or more additional therapeutic agent(s). In certain such embodiments, the conjoint administration provides an additive effect, wherein an additive effect refers to the sum of each of the effects of individual administration of the compound of the invention and the one or more additional therapeutic agent(s).

In certain embodiments, the process for forming a pharmaceutical composition of the invention comprises a. dissolving a crystalline form of the invention (such as crystalline form A, crystalline form H, crystalline form E, crystalline form G, crystalline form B, or crystalline form C) in a solvent to form a solution; and b. preparing the pharmaceutical composition from the solution. In some aspects, the preparing the pharmaceutical composition from the solution comprises spray-drying the solution, and formulating the spray-dried solution into a solid dosage form. In some embodiments, the present invention is directed to the pharmaceutical composition prepared by said process. In some embodiments, the crystalline form is form A. In some embodiments, the crystalline form is form H. In some embodiments, the crystalline form is form E. In some embodiments, the crystalline form is form G. In some embodiments, the crystalline form is form B. In some embodiments, the crystalline form is form C.

Any crystalline form described herein, including any crystalline form described in any aspect, embodiment or example of this application, can be used in any process of the invention described herein.

Methods of Treatment

The non-selective $Ca^{2+-}$ permeable Transient Receptor Potential (TRP) channels act as sensors that transduce extracellular cues to the intracellular environment in diverse cellular processes, including actin remodeling and cell migration (Greka et al., Nat Neurosci 6, 837-845, 2003; Ramsey et al., Annu Rev Physiol 68, 619-647, 2006; Montell, Pflugers Arch 451, 19-28, 2005; Clapham, Nature 426, 517-524, 2003). Dynamic rearrangement of the actin cytoskeleton relies on spatiotemporally regulated $Ca^{2+}$ influx (Zheng and Poo, Annu Rev Cell Dev Biol 23, 375-404, 2007); Brandman and Meyer, Science 322, 390-395, 2008); Collins and Meyer, Dev Cell 16, 160-161, 2009) and the small GTPases RhoA and Racl serve as key modulators of these changes (Etienne-Manneville and Hall, Nature 420, 629-635, 2002); Raftopoulou and Hall, Dev Biol 265, 23-32, 2004). RhoA induces stress fiber and focal adhesion formation, while Racl mediates lamellipodia formation (Etienne-Manneville and Hall, Nature 420, 629-635, 2002). The Transient Receptor Potential Cation Channel, subfamily C, member 5 (TRPC5) acts in concert with TRPC6 to regulate Ca2+ influx, actin remodeling, and cell motility in kidney podocytes and fibroblasts. TRPC5-mediated $Ca^{2+}$ influx increases Racl activity, whereas TRPC6-mediated Ca2+ influx promotes RhoA activity. Gene silencing of TRPC6 channels abolishes stress fibers and diminishes focal contacts, rendering a motile, migratory cell phenotype. In contrast, gene silencing of TRPC5 channels rescues stress fiber formation, rendering a contractile cell phenotype. The results described herein unveil a conserved signaling mechanism whereby TRPC5 and TRPC6 channels control a tightly regulated balance of cytoskeletal dynamics through differential coupling to Racl and RhoA.

$Ca^{2+}$-dependent remodeling of the actin cytoskeleton is a dynamic process that drives cell migration (Wei et al., Nature 457, 901-905, 2009). RhoA and Racl act as switches responsible for cytoskeletal rearrangements in migrating cells (Etienne-Manneville and Hall, Nature 420, 629-635, 2002); Raftopoulou and Hall, Dev Biol 265, 23-32, 2004). Activation of Racl mediates a motile cell phenotype, whereas RhoA activity promotes a contractile phenotype (Etienne-Manneville and Hall, Nature 420, 629-635, 2002). $Ca^{2+}$ plays a central role in small GTPase regulation (Aspenstrom et al., Biochem J 377, 327-337, 2004). Spatially and temporally restricted flickers of $Ca^{2+}$ are enriched near the leading edge of migrating cells (Wei et al., Nature 457, 901-905, 2009). Ca2+microdomains have thus joined local bursts in Racl activity (Gardiner et al., Curr Biol 12, 2029-2034, 2002; Machacek et al., Nature 461, 99-103, 2009) as critical events at the leading edge. To date, the sources of Ca2+ influx responsible for GTPase regulation remain largely elusive. TRP (Transient Receptor Potential) channels generate time and space-limited $Ca^{2+}$ signals linked to cell migration in fibroblasts and neuronal growth cones0. Specifically, TRPC5 channels are known regulators of neuronal growth cone guidancel and their activity in neurons is dependent on PI3K and Racl activity (Bezzerides et al., Nat Cell Biol 6, 709-720, 2004).

Podocytes are neuronal-like cells that originate from the metanephric mesenchyme of the kidney glomerulus and are essential to the formation of the kidney filtration apparatus (Somlo and Mundel, Nat Genet. 24, 333-335, 2000; Fukasawa et al., J Am Soc Nephrol 20, 1491-1503, 2009). Podocytes possess an exquisitely refined repertoire of cytoskeletal adaptations to environmental cues (Somlo and Mundel, Nat Genet 24, 333-335, 2000; Garg et al., Mol Cell Biol 27, 8698-8712, 2007; Verma et al., J Clin Invest 116, 1346-1359, 2006; Verma et al., J Biol Chem 278, 20716-20723, 2003; Barletta et al., J Biol Chem 278, 19266-19271, 2003; Holzman et al., Kidney Int 56, 1481-1491, 1999; Ahola et al., Am J Pathol 155, 907-913, 1999; Tryggvason and Wartiovaara, N Engl J Med 354, 1387-1401, 2006; Schnabel and Farquhar, J Cell Biol 111, 1255-1263, 1990; Kurihara et al., Proc Natl Acad Sci USA 89, 7075-7079, 1992). Early events of podocyte injury are characterized by dysregulation of the actin cytoskeleton (Faul et al., Trends Cell Biol 17, 428-437, 2007; Takeda et al., J Clin Invest 108, 289-301, 2001; Asanuma et al., Nat Cell Biol 8, 485-491, 2006) and Ca2+ homeostasis (Hunt et al., J Am Soc Nephrol 16, 1593-1602, 2005; Faul et al., Nat Med 14, 931-938, 2008). These changes are associated with the onset of proteinuria, the loss of albumin into the urinary space, and ultimately kidney failure (Tryggvason and Wartiovaara, N Engl J Med 354, 1387-1401, 2006). The vasoactive hormone Angiotensin II induces $Ca^{2+}$ influx in podocytes, and prolonged treatment results in loss of stress fibers (Hsu et al., J Mol Med 86, 1379-1394, 2008). While there is a recognized link between Ca2+ influx and cytoskeletal reorganization, the mechanisms by which the podocyte senses and transduces extracellular cues that modulate cell shape and motility remain elusive. TRP Canonical 6 (TRPC6) channel mutations have been linked to podocyte injury (Winn et al., Science 308, 1801-1804, 2005; Reiser et al., Nat Genet 37, 739-744, 2005; Moller et al., J Am Soc Nephrol 18, 29-36, 2007; Hsu et al., Biochim Biophys Acta 1772, 928-936, 2007), but little is known about the specific pathways that regulate this process. Moreover, TRPC6 shares close homology with six other members of the TRPC channel family (Ramsey et al., Annu Rev Physiol 68, 619-647, 2006; Clapham, Nature 426, 517-524, 2003). TRPC5 channels antagonize TRPC6 channel activity to control a tightly regulated balance of cytoskeletal dynamics through differential coupling to distinct small GTPases.

Proteinuria

Proteinuria is a pathological condition wherein protein is present in the urine. Albuminuria is a type of proteinuria. Microalbuminuria occurs when the kidney leaks small amounts of albumin into the urine. In a properly functioning body, albumin is not normally present in urine because it is retained in the bloodstream by the kidneys. Microalbuminuria is diagnosed either from a 24-hour urine collection (20 to 200 μg/min) or, more commonly, from elevated concentrations (30 to 300 mg/L) on at least two occasions. Microalbuminuria can be a forerunner of diabetic nephropathy. An albumin level above these values is called macroalbuminuria. Subjects with certain conditions, e.g., diabetic nephropathy, can progress from microalbuminuria to macroalbuminuria and reach a nephrotic range (>3.5 g/24 hours) as kidney disease reaches advanced stages.

Causes of Proteinuria

Proteinuria can be associated with a number of conditions, including focal segmental glomerulosclerosis, IgA nephropathy, diabetic nephropathy, lupus nephritis, membranoproliferative glomerulonephritis, progressive (crescentic) glomerulonephritis, and membranous glomerulonephritis.

A. Focal Segmental Glomerulosclerosis (FSGS)

Focal Segmental Glomerulosclerosis (FSGS) is a disease that attacks the kidney's filtering system (glomeruli) causing serious scarring. FSGS is one of the many causes of a disease known as Nephrotic Syndrome, which occurs when protein in the blood leaks into the urine (proteinuria).

Very few treatments are available for patients with FSGS. Many patients are treated with steroid regimens, most of which have very harsh side effects. Some patients have shown to respond positively to immunosuppressive drugs as well as blood pressure drugs which have shown to lower the level of protein in the urine. To date, there is no commonly accepted effective treatment or cure and there are no FDA approved drugs to treat FSGS. Therefore, more effective methods to reduce or inhibit proteinuria are desirable.

B. IgA Nephropathy

IgA nephropathy (also known as IgA nephritis, IgAN, Berger's disease, and synpharyngitic glomerulonephritis) is a form of glomerulonephritis (inflammation of the glomeruli of the kidney). IgA nephropathy is the most common glomerulonephritis throughout the world. Primary IgA nephropathy is characterized by deposition of the IgA antibody in the glomerulus. There are other diseases associated with glomerular IgA deposits, the most common being Henoch-Schönlein purpura (HSP), which is considered by many to be a systemic form of IgA nephropathy. Henoch-Schönlein purpura presents with a characteristic purpuric skin rash, arthritis, and abdominal pain and occurs more commonly in young adults (16-35 yrs old). HSP is associated with a more benign prognosis than IgA nephropathy. In IgA nephropathy there is a slow progression to chronic renal failure in 25-30% of cases during a period of 20 years.

C. Diabetic Nephropathy

Diabetic nephropathy, also known as Kimmelstiel-Wilson syndrome and intercapillary glomerulonephritis, is a progressive kidney disease caused by angiopathy of capillaries in the kidney glomeruli. It is characterized by nephrotic syndrome and diffuse glomerulosclerosis. It is due to long-standing diabetes mellitus and is a prime cause for dialysis. The earliest detectable change in the course of diabetic nephropathy is a thickening in the glomerulus. At this stage, the kidney may start allowing more serum albumin than normal in the urine. As diabetic nephropathy progresses, increasing numbers of glomeruli are destroyed by nodular glomerulosclerosis and the amount of albumin excreted in the urine increases.

D. Lupus Nephritis

Lupus nephritis is a kidney disorder that is a complication of systemic lupus erythematosus. Lupus nephritis occurs when antibodies and complement build up in the kidneys, causing inflammation. It often causes proteinuria and may progress rapidly to renal failure. Nitrogen waste products build up in the bloodstream. Systemic lupus erythematosus causes various disorders of the internal structures of the kidney, including interstitial nephritis. Lupus nephritis affects approximately 3 out of 10,000 people.

E. Membranoproliferative Glomerulonephritis I/II/III

Membranoproliferative glomerulonephritis is a type of glomerulonephritis caused by deposits in the kidney glomerular mesangium and basement membrane thickening, activating complement and damaging the glomeruli. There are three types of membranoproliferative glomerulonephritis. Type I is caused by immune complexes depositing in the kidney and is believed to be associated with the classical complement pathway. Type II is similar to Type I, however, it is believed to be associated with the alternative complement pathway. Type III is very rare and it is characterized by a mixture of subepithelial deposits and the typical pathological findings of Type I disease.

F. Progressive (Crescentic) Glomerulonephritis

Progressive (crescentic) glomerulonephritis (PG) is a syndrome of the kidney that, if left untreated, rapidly progresses into acute renal failure and death within months. In 50% of cases, PG is associated with an underlying disease such as Goodpasture's syndrome, systemic lupus erythematosus, or Wegener granulomatosis; the remaining cases are idiopathic. Regardless of the underlying cause, PG involves severe injury to the kidney's glomeruli, with many of the glomeruli containing characteristic crescent-shaped scars. Patients with PG have hematuria, proteinuria, and occasionally, hypertension and edema. The clinical picture is consistent with nephritic syndrome, although the degree of proteinuria may occasionally exceed 3 g/24 hours, a range associated with nephrotic syndrome. Untreated disease may progress to decreased urinary volume (oliguria), which is associated with poor kidney function.

G. Membranous Glomerulonephritis

Membranous glomerulonephritis (MGN) is a slowly progressive disease of the kidney affecting mostly patients between ages of 30 and 50 years, usually Caucasian. It can develop into nephrotic syndrome. MGN is caused by circulating immune complex. Current research indicates that the majority of the immune complexes are formed via binding of antibodies to antigens in situ to the glomerular basement membrane. The said antigens may be endogenous to the basement membrane, or deposited from systemic circulation.

H. Alport Syndrome

Alport syndrome is a genetic disorder affecting around 1 in 5,000-10,000 children, characterized by glomerulonephritis, end-stage kidney disease, and hearing loss. Alport syndrome can also affect the eyes, though the changes do not usually affect sight, except when changes to the lens occur in later life. Blood in urine is universal. Proteinuria is a feature as kidney disease progresses.

I. Hypertensive Kidney Disease

Hypertensive kidney disease (Hypertensive nephrosclerosis (HN or HNS) or hypertensive nephropathy (HN)) is a medical condition referring to damage to the kidney due to chronic high blood pressure. HN can be divided into two types: benign and malignant. Benign nephrosclerosis is common in individuals over the age of 60 while malignant nephrosclerosis is uncommon and affects 1-5% of individuals with high blood pressure, that have diastolic blood pressure passing 130 mm Hg. Signs and symptoms of chronic kidney disease, including loss of appetite, nausea, vomiting, itching, sleepiness or confusion, weight loss, and an unpleasant taste in the mouth, may develop. Chronic high blood pressure causes damages to kidney tissue; this includes the small blood vessels, glomeruli, kidney tubules and interstitial tissues. The tissue hardens and thickens which is known as nephrosclerosis. The narrowing of the blood vessels means less blood is going to the tissue and so less oxygen is reaching the tissue resulting in tissue death (ischemia).

J. Nephrotic Syndrome

Nephrotic syndrome is a collection of symptoms due to kidney damage. This includes protein in the urine, low blood albumin levels, high blood lipids, and significant swelling. Other symptoms may include weight gain, feeling tired, and foamy urine. Complications may include blood clots, infections, and high blood pressure. Causes include a number of kidney diseases such as focal segmental glomerulosclerosis, membranous nephropathy, and minimal change disease. It may also occur as a complication of diabetes or lupus. The underlying mechanism typically involves damage to the glomeruli of the kidney. Diagnosis is typically based on urine testing and sometimes a kidney biopsy. It differs from nephritic syndrome in that there are no red blood cells in the urine. Nephrotic syndrome is characterized by large amounts of proteinuria (>3.5 g per 1.73 m2 body surface area per day, or >40 mg per square meter body surface area per hour in children), hypoalbuminemia (<2.5 g/dl), hyperlipidaemia, and edema that begins in the face. Lipiduria (lipids in urine) can also occur, but is not essential for the diagnosis of nephrotic syndrome. Hyponatremia also occur with a low fractional sodium excretion. Genetic forms of nephrotic syndrome are typically resistant to steroid and other immunosuppressive treatment. Goals of therapy are to control urinary protein loss and swelling, provide good nutrition to allow the child to grow, and prevent complications. Early and aggressive treatment are used to control the disorder.

K. Minimal Change Disease

Minimal change disease (also known as MCD, minimal change glomerulopathy, and nil disease, among others) is a disease affecting the kidneys which causes a nephrotic syndrome. The clinical signs of minimal change disease are proteinuria (abnormal excretion of proteins, mainly albumin, into the urine), edema (swelling of soft tissues as a consequence of water retention), weight gain, and hypoalbuminaemia (low serum albumin). These signs are referred to collectively as nephrotic syndrome. The first clinical sign of minimal change disease is usually edema with an associated increase in weight. The swelling may be mild but patients can present with edema in the lower half of the body, periorbital edema, swelling in the scrotal/labial area and anasarca in more severe cases. In older adults, patients may also present with acute kidney injury (20-25% of affected adults) and high blood pressure. Due to the disease process, patients with minimal change disease are also at risk of blood clots and infections.

L. Membranous Nephropathy

Membranous nephropathy refers to the deposition of immune complexes on the glomerular basement membrane (GBM) with GBM thickening. The cause is usually unknown (idiopathic), although secondary causes include drugs, infections, autoimmune disorders, and cancer. Manifestations include insidious onset of edema and heavy proteinuria with benign urinary sediment, normal renal function, and normal or elevated blood pressure. Membranous nephropathy is diagnosed by renal biopsy. Spontaneous remission is common. Treatment of patients at high risk of progression is usually with corticosteroids and cyclophosphamide or chlorambucil.

M. Postinfectious Glomerulonephritis

Acute proliferative glomerulonephritis is a disorder of the glomeruli (glomerulonephritis), or small blood vessels in the kidneys. It is a common complication of bacterial infections, typically skin infection by *Streptococcus* bacteria types 12, 4 and 1 (impetigo) but also after streptococcal pharyngitis, for which it is also known as postinfectious or poststreptococcal glomerulonephritis. It can be a risk factor for future albuminuria. In adults, the signs and symptoms of infection may still be present at the time when the kidney problems develop, and the terms infection-related glomerulonephritis or bacterial infection-related glomerulonephritis are also used. Acute glomerulonephritis resulted in 19,000 deaths in 2013 down from 24,000 deaths in 1990 worldwide. Acute proliferative glomerulonephritis (post-streptococcal glomerulonephritisis) is caused by an infection with *streptococcus* bacteria, usually three weeks after infection, usually of the pharynx or the skin, given the time required to raise antibodies and complement proteins. The infection causes blood vessels in the kidneys to develop inflammation, this hampers the renal organs ability to filter urine. [citation needed] Acute proliferative glomerulonephritis most commonly occurs in children.

N. Thin Basement Membrane Disease

Thin basement membrane disease (TBMD, also known as benign familial hematuria and thin basement membrane nephropathy or TBMN) is, along with IgA nephropathy, the most common cause of hematuria without other symptoms. The only abnormal finding in this disease is a thinning of the basement membrane of the glomeruli in the kidneys. Its importance lies in the fact that it has a benign prognosis, with patients maintaining a normal kidney function throughout their lives. Most patients with thin basement membrane disease are incidentally discovered to have microscopic hematuria on urinalysis. The blood pressure, kidney function, and the urinary protein excretion are usually normal. Mild proteinuria (less than 1.5 g/day) and hypertension are seen in a small minority of patients. Frank hematuria and loin pain should prompt a search for another cause, such as kidney stones or loin pain-hematuria syndrome. Also, there are no systemic manifestations, so presence of hearing impairment or visual impairment should prompt a search for hereditary nephritis such as Alport syndrome. Some individuals with TBMD are thought to be carriers for genes that cause Alport syndrome.

O. Mesangial Proliferative Glomerulonephritis

Mesangial proliferative glomerulonephritis is a form of glomerulonephritis associated primarily with the mesangium. There is some evidence that interleukin-10 may inhibit it in an animal model. [2] It is classified as type II lupus nephritis by the World Health Organization (WHO). Mesangial cells in the renal glomerulus use endocytosis to take up and degrade circulating immunoglobulin. This normal process stimulates mesangial cell proliferation and matrix deposition. Therefore, during times of elevated circulating immunoglobulin (i.e. lupus and IgA nephropathy) one would expect to see an increased number of mesangial cells and matrix in the glomerulus. This is characteristic of nephritic syndromes.

P. Amyloidosis (Primary)

Amyloidosis is a group of diseases in which abnormal protein, known as amyloid fibrils, builds up in tissue. [4] Symptoms depend on the type and are often variable. [2] They may include diarrhea, weight loss, feeling tired, enlargement of the tongue, bleeding, numbness, feeling faint with standing, swelling of the legs, or enlargement of the spleen. [2] There are about 30 different types of amyloidosis, each due to a specific protein misfolding. [5] Some are genetic while others are acquired. [3] They are grouped into localized and systemic forms. [2] The four most common types of systemic disease are light chain (AL), inflammation (AA), dialysis (Aβ2M), and hereditary and old age (ATTR). Primary amyloidosis refers to amyloidosis in which no associaited clinical condition is identified.

Q. c1q Nephropathy

C1q nephropathy is a rare glomerular disease with characteristic mesangial C1q deposition noted on immunofluorescence microscopy. It is histologically defined and poorly understood. Light microscopic features are heterogeneous and comprise minimal change disease (MCD), focal segmental glomerulosclerosis (FSGS), and proliferative glomerulonephritis. Clinical presentation is also diverse, and ranges from asymptomatic hematuria or proteinuria to frank nephritic or nephrotic syndrome in both children and adults. Hypertension and renal insufficiency at the time of diagnosis are common findings. Optimal treatment is not clear and is usually guided by the underlying light microscopic lesion. Corticosteroids are the mainstay of treatment, with immunosuppressive agents reserved for steroid resistant cases. The presence of nephrotic syndrome and FSGS appear to predict adverse outcomes as opposed to favorable outcomes in those with MCD. (Devasahayam, et al., "C1q Nephropathy: The Unique Underrecognized Pathological Entity," Analytical Cellular Pathology, vol. 2015, Article ID 490413, 5 pages, 2015. doi.org/10.1155/2015/490413.)

Anti-glomerular basement membrane (GBM) disease, also known as Goodpasture's disease, is a rare condition that causes inflammation of the small blood vessels in the kidneys and lungs. The antiglomerular basement membrane (GBM) antibodies primarily attack the kidneys and lungs, although, generalized symptoms like malaise, weight loss, fatigue, fever, and chills are also common, as are joint aches and pains. 60 to 80% of those with the condition experience both lung and kidney involvement; 20-40% have kidney involvement alone, and less than 10% have lung involvement alone. Lung symptoms usually antedate kidney symptoms and usually include: coughing up blood, chest pain (in less than 50% of cases overall), cough, and shortness of breath. Kidney symptoms usually include blood in the urine, protein in the urine, unexplained swelling of limbs or face, high amounts of urea in the blood, and high blood pressure. GPS causes the abnormal production of anti-GBM antibodies, by the plasma cells of the blood. The anti-GBM antibodies attack the alveoli and glomeruli basement membranes. These antibodies bind their reactive epitopes to the basement membranes and activate the complement cascade, leading to the death of tagged cells. T cells are also implicated. It is generally considered a type II hypersensitivity reaction.

Measurement of Urine Protein Levels

Protein levels in urine can be measured using methods known in the art. Until recently, an accurate protein measurement required a 24-hour urine collection. In a 24-hour collection, the patient urinates into a container, which is kept refrigerated between trips to the bathroom. The patient is instructed to begin collecting urine after the first trip to the bathroom in the morning. Every drop of urine for the rest of the day is to be collected in the container. The next morning, the patient adds the first urination after waking and the collection is complete.

More recently, researchers have found that a single urine sample can provide the needed information. In the newer technique, the amount of albumin in the urine sample is compared with the amount of creatinine, a waste product of normal muscle breakdown. The measurement is called a urine albumin-to-creatinine ratio (UACR). A urine sample containing more than 30 milligrams of albumin for each gram of creatinine (30 mg/g) is a warning that there may be a problem. If the laboratory test exceeds 30 mg/g, another UACR test should be performed 1 to 2 weeks later. If the second test also shows high levels of protein, the person has persistent proteinuria, a sign of declining kidney function, and should have additional tests to evaluate kidney function.

Tests that measure the amount of creatinine in the blood will also show whether a subject's kidneys are removing wastes efficiently. Too much creatinine in the blood is a sign that a person has kidney damage. A physician can use the creatinine measurement to estimate how efficiently the kidneys are filtering the blood. This calculation is called the estimated glomerular filtration rate, or eGFR. Chronic kidney disease is present when the eGFR is less than 60 milliliters per minute (mL/min).

TRPC5

TRPC is a family of transient receptor potential cation channels in animals. TRPC5 is subtype of the TRPC family of mammalian transient receptor potential ion channels. Three examples of TRPC5 are human (Gen Bank Accession Nos. NM_012471.2 and NP_036603.1; Gene ID 7224); mouse (Gen Bank Accession Nos. NM_009428.2 and NP_033454.1; Gene ID 22067); and rat (Gen Bank Accession Nos. NM_080898.2 and NP_543174.1; Gene ID 140933). TRPC1

TRPC1 is an ion channel located on the plasma membrane of numerous human and animal cell types. It is a nonspecific cation channel, which means that both sodium and calcium ions can pass through it. TRPC1 is thought to mediate calcium entry in response to depletion of endoplasmic calcium stores or activation of receptors coupled to the phospholipase C system. In HEK293 cells the unitary current-voltage relationship of endogenous TRPC1 channels is almost linear, with a slope conductance of about 17 pS. The extrapolated reversal potential of TRPC1 channels is +30 mV. The TRPC1 protein is widely expressed throughout the mammalian brain and has a similar corticolimbic expression pattern as TRPC4 and TRPC5. The highest density of TRPC1 protein is found in the lateral septum, an area with dense TRPC4 expression, and hippocampus and prefrontal cortex, areas with dense TRPC5 expression.

TRPC4

TRPC4 is a member of the transient receptor potential cation channels. This protein forms a non-selective calcium-permeable cation channel that is activated by Gαi-coupled receptors, Gαq-coupled receptors and tyrosine kinases, and plays a role in multiple processes including endothelial permeability, vasodilation, neurotransmitter release and cell proliferation. The nonselective cation channel TrpC4 has been shown to be present in high abundance in the corticolimbic regions of the brain. In addition, TRPC4 mRNA is present in midbrain dopaminergic neurons in the ventral tegmental area and the substantia nigra. Deletion of the trpc4 gene decreases levels of sociability in a social exploration task. These results suggest that TRPC4 may play a role in regulating social anxiety in a number of different disorders. TRPC4 has been shown to interact with TRPC1 and TRPC5.

The invention therefore provides methods of inhibiting one or more of TRPC1, TRPC4, and TRPC5 ion channels, or ion channels comprising a tetrameric combination of any of TRPC1, TRPC4, and TRPC5, in a subject in need thereof, comprising administering to the subject an effective amount of a pharmaceutical composition of Compound 100 as described herein. "Ion channels comprising a tetrameric combination of any of TRPC1, TRPC4, and TRPC5" ion channels can contain any combination of TRPC1, TRPC4, and TRPC5 ion channels. In some embodiments, the ion channel to be inhibited is a heterotetrameric form comprising a combination of one or more TRPC1 ion channels with one or more TRPC4 and/or TRPC5 ion channels. In some embodiments, the ion channel to be inhibited is a heterotetrameric form comprising a combination of one or more TRPC1 ion channels with one or more TRPC4 and/or TRPC5 ion channels. In some embodiments, the ion channel to be inhibited is a heterotetrameric form comprising one or more TRPC4 ion channels and one or more TRPC5 ion channels. The heterotetrameric form can comprise any combination of TRPC1, TRPC4, and TRPC5 ion channels. In some embodiments, the heterotetrameric form is TRPC1: TRPC4:TRPC4:TRPC5, TRPC1: TRPC1: TRPC5: TRPC5, TRPC4: TRPC4: TRPC5: TRPC5, or TRPC4: TRPC5: TRPC5: TRPC5.

In some embodiments, the subject requiring inhibition of ion channels comprising a tetrameric combination of any of TRPC1, TRPC4, and TRPC5 is suffering from a kidney disease, a nephropathy associated with a disease or condition, pain, anxiety, or depression. In some embodiments, the pain is selected form neuropathic pain and visceral pain. In embodiments, the cancer is selected from chemoresistant breast carcinoma, adriamycin-resistant breast cancer, chemoresistant colorectal cancer, medulloblastoma, and tumor angiogenesis.

In certain embodiments, the invention provides methods for treating, or the reducing the severity risk of developing, a disease or condition selected from kidney disease, a nephropathy associated with a disease or condition, pain, anxiety, or depression comprising administering to a subject in need thereof a therapeutically effective amount of a pharmaceutical composition comprising a crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one described herein.

In some embodiments, the disease or condition is kidney disease or a neuropathy associated with a condition or disease selected from Focal Segmental Glomerulosclerosis (FSGS), Diabetic nephropathy, Alport syndrome, hypertensive kidney disease, nephrotic syndrome, steroid-resistant nephrotic syndrome, minimal change disease, membranous nephropathy, idiopathic membranous nephropathy, membranoproliferative glomerulonephritis (MPGN), immune complex-mediated MPGN, complement-mediated MPGN, Lupus nephritis, postinfectious glomerulonephritis, thin basement membrane disease, mesangial proliferative glomerulonephritis, amyloidosis (primary), c1q nephropathy, rapidly progressive GN, anti-GBM disease, C3 glomerulonephritis, hypertensive nephrosclerosis, IgA nephropathy, IgG4 nephropathy, proteinuric kidney disease, microalbuminuria, macroalbuminuria kidney disease, transplant-related FSGS, transplant-related nephrotic syndrome, transplant-related proteinuria, nodular glomerulonephritis, NASR disease (proliferative glomerulonephritis with monoclonal IgG deposits), polycystic kidney disease, autosomal dominant polycystic kidney disease (ADPKD), autosomal recessive polycystic kidney disease (ARPKD), or an nephropathy associated with any one of obesity, insulin resistance, Type II diabetes, prediabetes, metabolic syndrome, dyslipidemia, Fabry's disease, pulmonary arterial hypertension, cholestatic liver disease, non-alcoholic fatty liver disease (NAFLD), non-alcoholic steatohepatitis (NASH), or cancer.

In some embodiment, the kidney disease or a neuropathy associated with a condition or disease is Focal Segmental Glomerulosclerosis (FSGS), Diabetic nephropathy, Alport syndrome, hypertensive kidney disease, obesity-related nephropathy, nephrotic syndrome, steroid-resistant nephrotic syndrome, minimal change disease, membranous nephropathy, membranoproliferative glomerulonephritis (MPGN), Lupus nephritis, postinfectious glomerulonephritis, thin basement membrane disease, mesangial proliferative glomerulonephritis, amyloidosis (primary), c1q nephropathy, anti-GBM disease, C3 glomerulonephritis, hypertensive nephrosclerosis, IgA nephropathy, IgG4 nephropathy, dyslipidemia associated with chronic kidney disease, nodular glomerulonephritis, NASR disease (proliferative glomerulonephritis with monoclonal IgG deposits), polycystic kidney disease, an nephropathy associated with Fabry's disease, or an nephropathy associated with metabolic syndrome.

In some embodiments, the kidney disease is proteinuric kidney disease. In some embodiments, the kidney disease is microalbuminuria or macroalbuminuria kidney disease.

In some embodiments, the disease or condition to be treated is nephropathy associated with pulmonary arterial hypertension.

In some embodiments, the disease or condition to be treated is pain selected from neuropathic pain and visceral pain.

In some embodiments, the disease or condition is nephropathy associated with a cancer selected from chemoresistant breast carcinoma, adriamycin-resistant breast cancer, chemoresistant colorectal cancer, medulloblastoma, and tumor angiogenesis.

The invention also provides methods of treating, or the reducing risk of developing, anxiety, or depression, or cancer, comprising administering to a subject in need thereof a therapeutically effective amount of a compound of the invention (e.g., a compound of Formula I), or a pharmaceutical composition comprising said compound.

In some embodiments, the disease or condition to be treated is transplant-related FSGS, transplant-related nephrotic syndrome, transplant-related proteinuria, cholestatic liver disease, polycystic kidney disease, autosomal dominant polycystic kidney disease (ADPKD), autosomal recessive polycystic kidney disease (ARPKD), obesity, insulin resistance, Type II diabetes, prediabetes, metabolic syndrome, non-alcoholic fatty liver disease (NAFLD), or non-alcoholic steatohepatitis (NASH).

In some embodiments, the kidney disease or a neuropathy associated with a condition or disease to be treated is hypertensive nephropathy, a nephropathy associated with metabolic syndrome, a nephropathy associated with obesity, a nephropathy associated with dyslipidemia, diabetic nephropathy, nephrotic syndrome, FSGS, or minimal change disease.

In some embodiments, the kidney disease or a neuropathy associated with a condition or disease to be treated is diabetic nephropathy, FSGS, or minimal change disease.

The invention also provides methods of treating, or the reducing risk of developing, anxiety, or depression, or cancer, comprising administering to a subject in need thereof a therapeutically effective amount of Compound 100, or a pharmaceutical composition comprising said compound.

Subjects to be treated by the methods of this invention are subjects who have been diagnosed with or are at risk of developing any of the diseases or symptoms set forth above. The methods are effective for a variety of subjects including mammals, e.g., humans and other animals, such as laboratory animals, e.g., mice, rats, rabbits, or monkeys, or domesticated and farm animals, e.g., cats, dogs, goats, sheep, pigs, cows, or horses. In some embodiments, the subject is a mammal. In some embodiments, the subject is a human.

EXAMPLES

Table of Abbreviations

| | |
|---|---|
| $a_w$ | water activity |
| EtOH | Ethanol |
| $H_2O$ | Water |
| DMSO | Dimethyl sulfoxide |
| XRPD | Powder X-ray Diffraction |
| DSC | Differential Scanning Calorimetry |
| TGA | Thermogravimetric Analysis |
| IPA | Isopropyl Alcohol |

Example 1. Preparation of Crystalline Form A

Method A

In a 100 mL, flask equipped with a magnetic stirrer, 1.0 g of 4-chloro-5-(4-(4-fluoro-2-(trifluoromethyl)phenoxy)-5,8-dihydropyrido[3,4-d]pyrimidin-7(6H)-yl)pyridazin-3(2H)-one was suspended into 15 mL of DMSO:EtOH (2:1). The slurry was stirred at RT for 0.5 h to allow complete dissolution. 15 mL of EtOH:$H_2O$ (1:1) was progressively added over a period of 2.0 hours. The resulting suspension was filtered and washed by 15 mL of EtOH:$H_2O$ (1:1) and dried at 50° C. under vacuum (−0.1 Mpa) for 3.5 hours to yield 0.83 g of white crystalline solid characterized as form A.

Method B

In a 100 mL, flask equipped with a magnetic stirrer, 1.0 g of 4-chloro-5-(4-(4-fluoro-2-(trifluoromethyl)phenoxy)-5,8-dihydropyrido[3,4-d]pyrimidin-7(6H)-yl)pyridazin-3(2H)-one was suspended into 15 mL of DMSO:EtOH (2:1). The slurry was stirred at RT for 0.5 h to allow complete dissolution. 0.3 mL of EtOH:$H_2O$ (1:1) was added followed by 0.03 g of form A seeds. The resulting mixture was stirred for 1.5 hours at room temperature. An additional 15 mL of EtOH:$H_2O$ (1:1) was then slowly added (0.5 mL/h for 1 h, followed by 1 mL/h for 1 h, then 2 mL/h for 1 h, and the remainder at 5 mL/h) at room temperature while maintaining stirring The resulting suspension was filtered and washed by 15 mL of EtOH:$H_2O$ (1:1) and dried at 50° C. under vacuum (−0.1 Mpa) for 3.5 hours to yield 0.7 g of white crystalline solid characterized as form A.

Figure 1B:
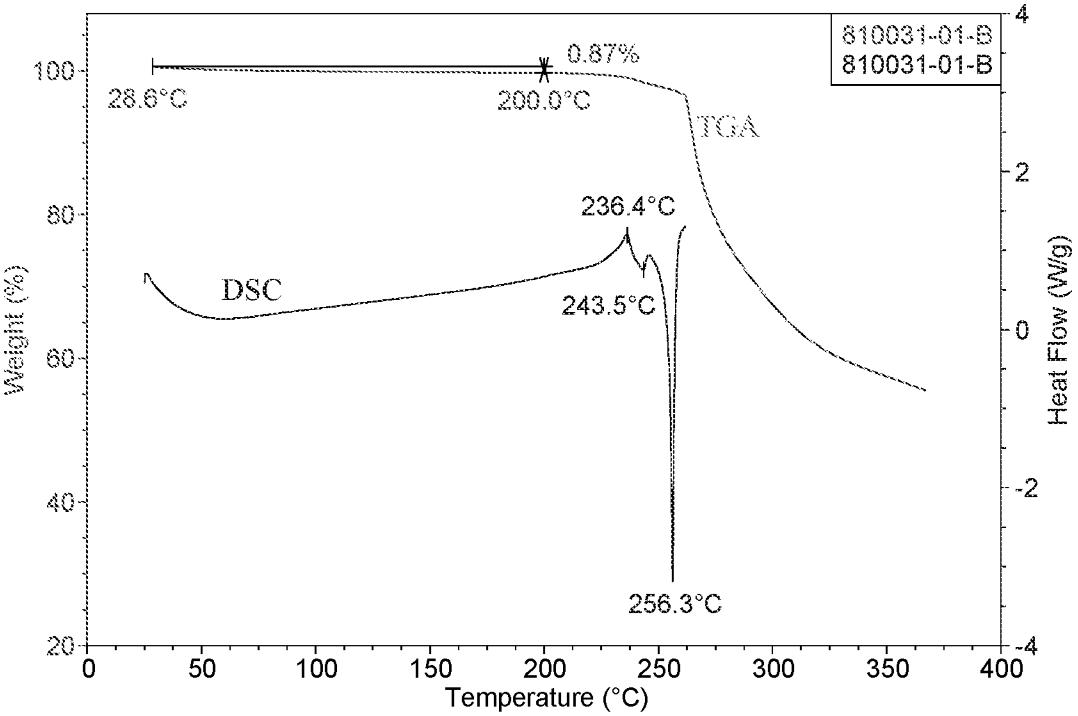
FIG. 1B shows experimental thermogravimetric analysis (TGA) and differential scanning calorimetry (DSC) data for crystalline form A of Compound 100.

Powder X-ray diffraction pattern and XRPD peaks with relative intensities of the crystalline form thus prepared are shown in FIG. 1A and Table 1, respectively. DSC and TGA data are shown in FIG. 1B.

TABLE 1

| XRPD Peak Listing of Form A | |
|---|---|
| °2-Theta | Relative Peak Height (%) |
| 4.4 | 61.6 |
| 8.8 | 12.1 |
| 9.2 | 14.3 |
| 11.7 | 73.3 |
| 12.3 | 18.0 |
| 13.3 | 16.8 |
| 14.2 | 26.3 |
| 14.7 | 13.2 |
| 16.0 | 22.3 |
| 16.9 | 47.0 |
| 17.8 | 100.0 |
| 19.6 | 11.5 |
| 21.0 | 9.0 |
| 22.2 | 14.6 |
| 22.7 | 24.3 |
| 24.2 | 11.1 |
| 25.6 | 19.0 |
| 27.6 | 64.1 |
| 28.0 | 41.2 |
| 30.3 | 8.2 |

Example 2. Preparation of Compound 100 Crystalline Form H

Method A

In a HPLC vial equipped with a stirring bar, 20 mg of 4-chloro-5-(4-(4-fluoro-2-(trifluoromethyl)phenoxy)-5,8-dihydropyrido[3,4-d]pyrimidin-7(6H)-yl)pyridazin-3 (2H)-one was suspended in 0.5 mL of a IPA/IPAc (1:1, v/v) mixture. The resulting slurry was magnetically stirred (~800 rpm) at 50° C. for about 3 days while keeping the vial closed. The slurry was cooled at room temperature and the solid isolated by centrifugation (10000 rpm, 2 min) and dried at RT for 24 hours to yield a white crystalline solid.

Method B

In a 20 mL glass vial, 1.0 g of 4-chloro-5-(4-(4-fluoro-2-(trifluoromethyl)phenoxy)-5,8-dihydropyrido[3,4-d]pyrimidin-7(6H)-yl)pyridazin-3(2H)-one was dissolved in mixture containing 10 mL of DMSO and 5 mL of IPA by stirring it at 50° C. for one hour. The resulting solution was filtered through a 0.45 μM PTFE membrane to obtain a clear solution and placed in a 100 mL flask. 2 mL of IPA was added followed by a few seeds of form H (obtained using method A), followed by an additional 103.3 mg of form H (obtained using method A). After 10 min of stirring at 50° C., 6 mL of IPA/$H_2O$ (1:1, v/v) was added over a period of 6 hours while maintaining the temperature at 50° C. Stirring was stopped and the suspension maintained at 50° C. for an additional 1.5 hours, before being cooled at 25° C. and kept at this temperature for 3 hours. The slurry was then filtered, and the resulting wet cake dried under vacuum for 12 hours. 0.77 g of form H (white crystalline solid) was obtained with a yield of ~67%.

Method C

In a 20 mL glass vial 1.5 g of 4-chloro-5-(4-(4-fluoro-2-(trifluoromethyl)phenoxy)-5,8-dihydropyrido[3,4-d]pyrimidin-7(6H)-yl)pyridazin-3(2H)-one was dissolved in 10 mL of DMSO by stirring it at 70° C. for an hours. The resulting solution was filtered through a 0.45 μM PTFE membrane to obtain a clear solution and placed in a 100 mL flask equipped with an overhead stirrer and stirred at 300 rpm at 70° C. 0.9 mL of an IPA/$H_2O$ (1:1, v/v) mixture was added followed by a few seeds of form H, followed by an additional addition of 75.3 mg of form H and 9.1 mL of IPA/$H_2O$ (1:1, v/v) over 6 hours. After stirring at 70° C. for an hour following the end of the addition of the IPA/$H_2O$, the suspension was cooled to 25° C. while maintaining stirring for 2 hours and then for an additional one hour without stirring. The suspension was filtered, and the resulting wet cake rinsed with 20 mL of IPA and then dried in a vacuum oven at 50° C. for 12 hours. 1.28 g of form H (white crystalline solid) was obtained with a yield of ~80%.

Figure 2B:
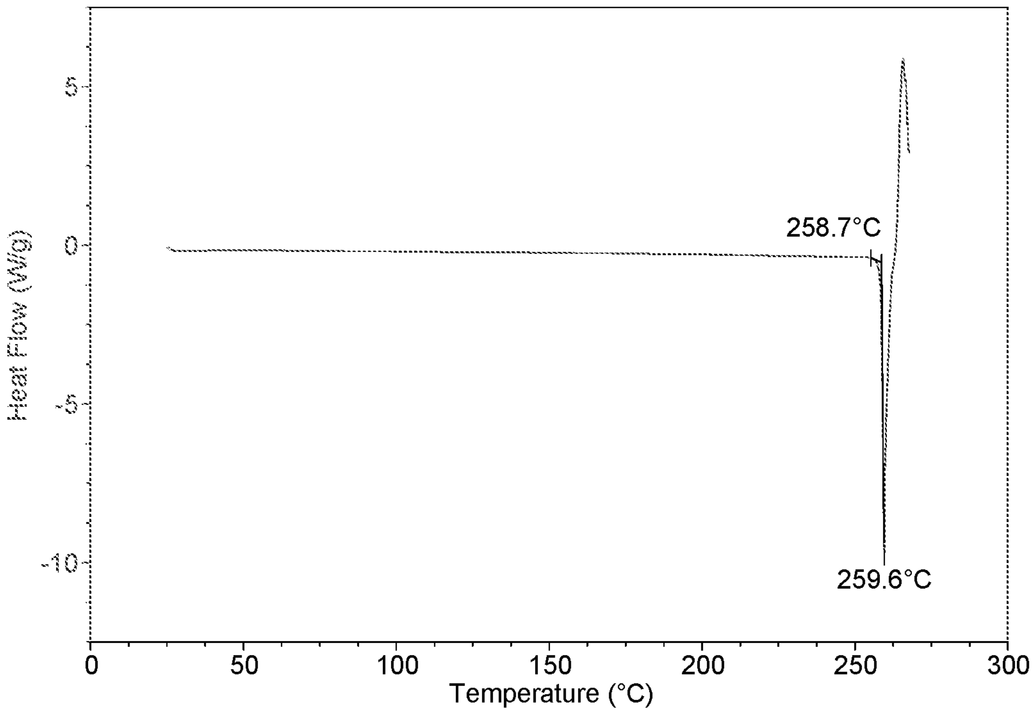
FIG. 2B shows experimental differential scanning calorimetry (DSC) data for crystalline form H of Compound 100 obtained via crystallization in a DMSO/IPA/$H_2O$ system.
Figure 2C:
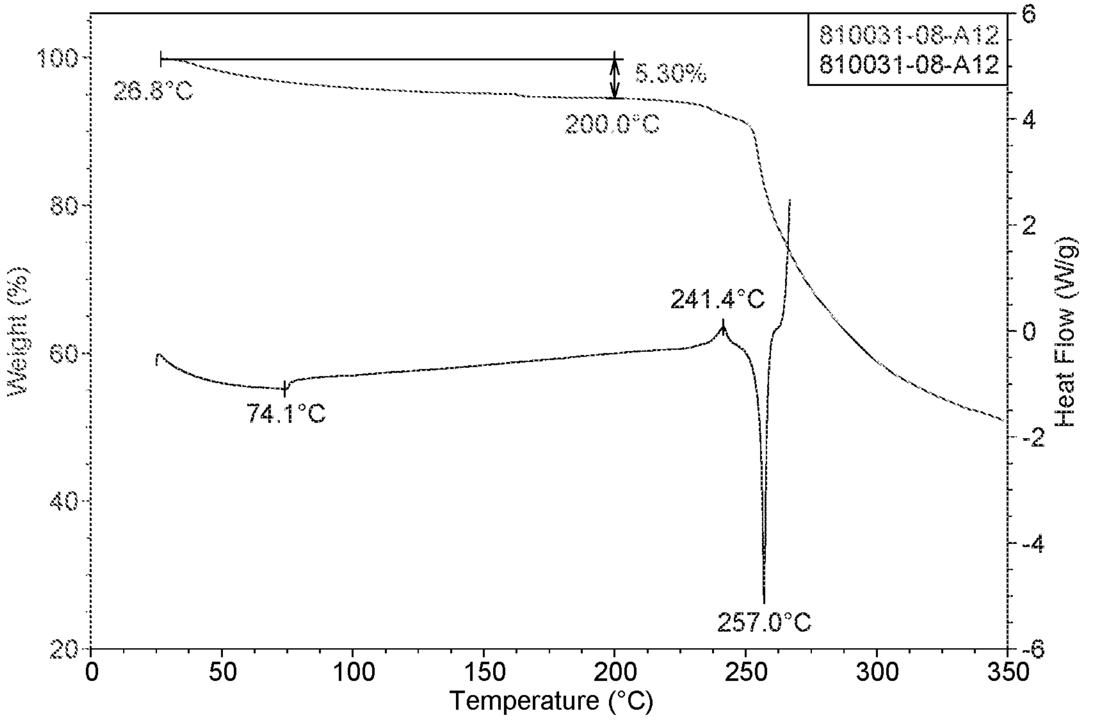
FIG. 2C shows experimental TGA and DSC data for crystalline form H of Compound 100 obtained via slurry of Compound 100 in IPA/IPAc (1:1, v/v) at 50° C.

Powder X-ray diffraction pattern and XRPD peaks with relative intensities of the crystalline form thus prepared are shown in FIG. 2A and Table 2, respectively. DSC data are shown in FIG. 2B.

TABLE 2

| XRPD Peak Listing of Compound 100 Crystalline Form H | |
|---|---|
| °2-Theta | Relative Peak Height (%) |
| 4.6 | 11.6 |
| 9.1 | 7.3 |
| 11.3 | 4.2 |
| 11.9 | 13.6 |
| 12.3 | 8.3 |
| 13.5 | 25.3 |
| 13.8 | 60.9 |
| 14.8 | 8.1 |
| 15.3 | 15.7 |
| 15.9 | 37.9 |
| 16.3 | 19.3 |
| 18.1 | 25.3 |
| 19.2 | 19.5 |
| 20.8 | 21.9 |
| 21.6 | 5.5 |
| 22.6 | 6.2 |
| 22.9 | 5.9 |
| 23.6 | 52.6 |
| 24.5 | 25.8 |
| 25.1 | 10.2 |
| 26.1 | 11.2 |
| 27.1 | 100.0 |
| 27.5 | 42.7 |
| 28.4 | 7.9 |
| 30.5 | 7.9 |
| 31.7 | 2.5 |
| 36.8 | 1.4 |

Example 3. Preparation of Compound 100 Crystalline Form E

About 15 mg of Compound 100 was suspended in 0.5 mL of DMF:$H_2O$ (1:9, v/v) in an HPLC vial. After the suspension was stirred for 3 days at room temperature, the remaining solids were then vacuum-dried at room temperature overnight. Alternatively, about 15 mg of Compound 100 was suspended in either 0.5 mL of DMSO:$H_2O$ (1:9, v/v) or DMF:$H_2O$ (1:1, v/v) to produce crystalline Form E. Yet another route to crystalline from E was through crystalline form C as described in Example 7.

Figure 3B:
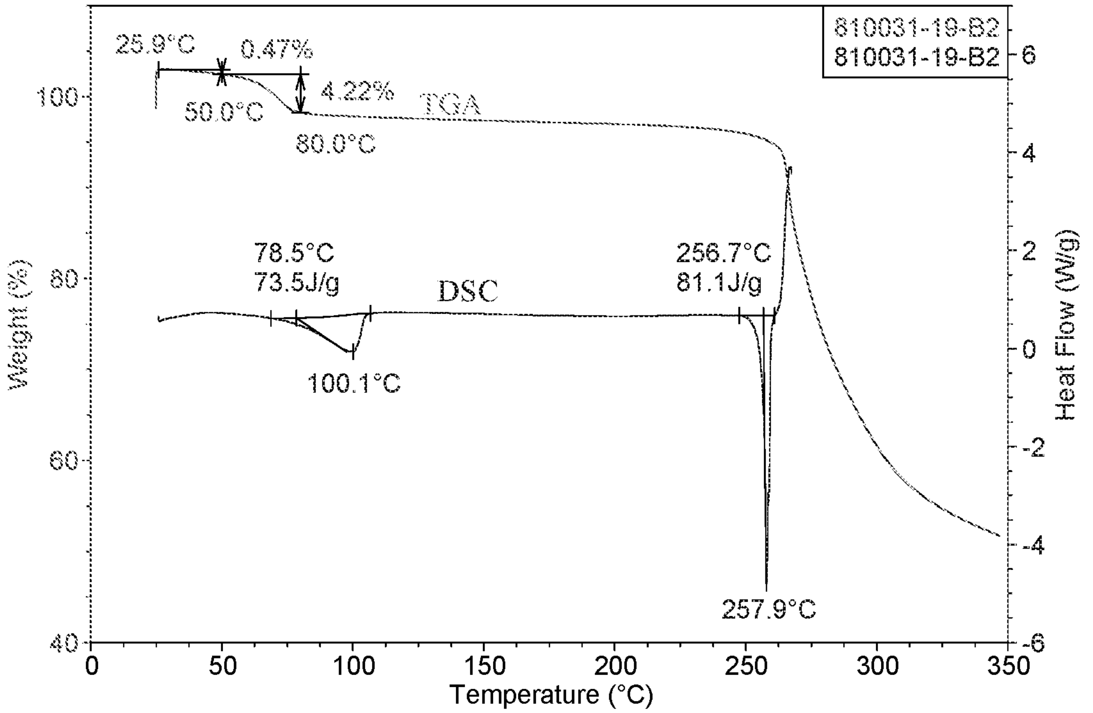
FIG. 3B shows experimental TGA and DSC data for crystalline form E of Compound 100.

Powder X-ray diffraction pattern and XRPD peaks with relative intensities of the crystalline form thus prepared are shown in FIG. 3A and Table 3, respectively. DSC and TGA data are shown in FIG. 3B.

TABLE 3

XRPD Peak Listing of Compound 100 Crystalline Form E

| °2-Theta | Relative Peak Height (%) |
|---|---|
| 11.7 | 63.8 |
| 14.4 | 30.0 |
| 15.2 | 100.0 |
| 15.6 | 26.5 |
| 17.0 | 24.2 |
| 17.8 | 15.0 |
| 18.3 | 19.0 |
| 19.6 | 41.1 |
| 20.2 | 32.0 |
| 20.7 | 12.7 |
| 24.0 | 22.1 |
| 24.8 | 55.0 |
| 26.2 | 47.8 |

Crystalline form E was also tested for stability at different relative humidities over 3-14 days. The results are shown below in Table 3.1

TABLE 3.1

Stability of Crystalline Form E at Different Relative Humidities (RH)

| Time | 30% RH | 50% RH | 60% RH | 92.5% RH |
|---|---|---|---|---|
| 3 days | Type E | Type E | Type E | Type E |
| 7 days | Type E | Type E | Type E | Type E |
| 14 days | Type E + Type F | Type E | Type E | Type E |

The appearance of Type F after storage of Type E for 14 days at 30% relative humidity indicated that Type E was unstable at such low relative humidity.

Example 4. Preparation of Compound 100 Crystalline Form G

Crystalline form G could be obtained via slurry of compound 100 in several solvent systems with $a_w \geq 0.8$. For example, compound 100 was slurried in acetonitrile/water (1:1, v/v) at room temperature to obtain form G.

Figure 4B:
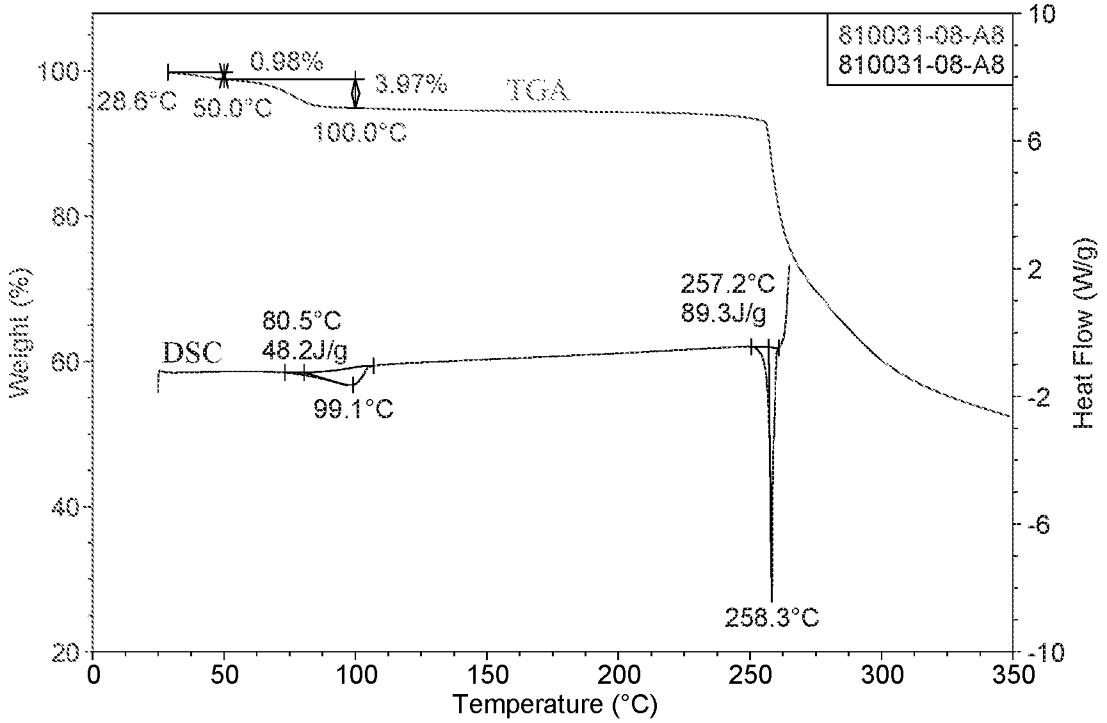
FIG. 4B shows experimental TGA and DSC data for crystalline form G of Compound 100.

Powder X-ray diffraction pattern and XRPD peaks with relative intensities of the crystalline form thus prepared are shown in FIG. 4A and Table 4, respectively. DSC and TGA data are shown in FIG. 4B.

TABLE 4

XRPD Peak Listing of Compound 100 Crystalline Form G

| °2-Theta | Relative Peak Height (%) |
|---|---|
| 7.9 | 11.3 |
| 11.8 | 28.3 |
| 12.9 | 14.1 |
| 14.4 | 17.0 |
| 15.0 | 37.7 |
| 15.3 | 52.4 |
| 15.8 | 34.4 |
| 16.7 | 14.3 |
| 17.4 | 15.5 |
| 19.5 | 27.0 |
| 19.7 | 28.0 |
| 20.2 | 24.7 |
| 20.6 | 36.9 |
| 23.2 | 15.8 |
| 23.6 | 5.6 |
| 23.9 | 31.8 |
| 24.6 | 43.5 |
| 25.3 | 28.4 |
| 25.9 | 100.0 |
| 26.3 | 29.7 |
| 28.6 | 16.4 |
| 30.2 | 6.1 |
| 32.0 | 6.8 |
| 36.9 | 6.8 |

Example 5. Preparation of Compound 100 Crystalline Form B

Crystal form B was obtained by heating Compound 100 to 244° C. and then cooling to room temperature with $N_2$ protection.

Alternatively, crystal form B was obtained by suspending approximately 30 mg of Compound 100 in 1.5 mL of a 2:1 (v/v) THF:heptane mixture at room temperature to form a slurry. The resulting wet cake was allowed to dry overnight resulting in crystal form B.

Figure 5B:
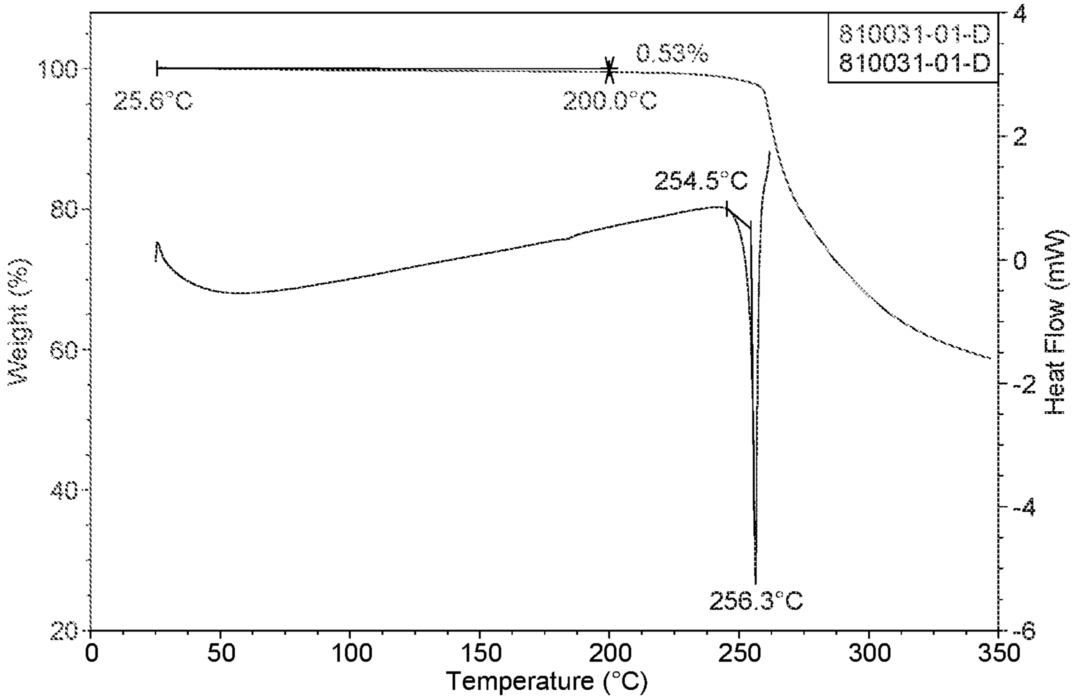
FIG. 5B shows experimental TGA and DSC data for crystalline form B of Compound 100.

Powder X-ray diffraction pattern and XRPD peaks with relative intensities of the crystalline form thus prepared are shown in FIG. 5A and Table 5, respectively. DSC and TGA data are shown in FIG. 5B.

TABLE 5

XRPD Peak Listing of Compound 100 Crystalline Form B

| °2-Theta | Relative Peak Height (%) |
|---|---|
| 4.40 | 100.0 |
| 8.74 | 17.8 |
| 9.13 | 9.9 |
| 11.67 | 24.4 |
| 12.51 | 27.8 |
| 13.10 | 19.8 |
| 13.64 | 14.1 |
| 14.03 | 27.8 |
| 16.26 | 26.2 |
| 16.93 | 18.6 |
| 17.48 | 47.9 |
| 17.72 | 41.4 |
| 18.46 | 30.9 |
| 20.51 | 7.6 |
| 21.89 | 18.5 |
| 23.97 | 20.5 |
| 24.79 | 10.6 |
| 27.49 | 39.2 |
| 27.86 | 25.5 |
| 31.76 | 6.1 |

Example 6. Preparation of Compound 100 Crystalline Form C

Crystal from C was prepared by dissolving Compound 100 in 1,4-dioxane and then adding anti-solvent $H_2O$ to the solution to precipitate out crystal from C.

Crystal form C was also prepared by the following anti-solvent crystallization procedure. Approximately 600 mg of Compound 100 crystal form A was dissolved in 70 mL THF at room temperature. To that solution was added 30 mL of heptane causing precipitation of material. The insoluble material was isolated as a wet cake and allowed to dry overnight, resulting in crystalline form C.

Once crystals of form C are isolated, they may be used as seeds in the following process to prepare additional crystal form C. One thousand mg of Compound 100 were suspended in 21 mL of a 2:1 (v/v) THF:$H_2O$ mixture at room temperature to which was added 3% (w/v) form C crystals. The components were mixed together (either mechanically or with a magnetic stir bar) overnight to form a slurry. The resulting wet cake was dried to produce crystalline form C.

Figure 6B:
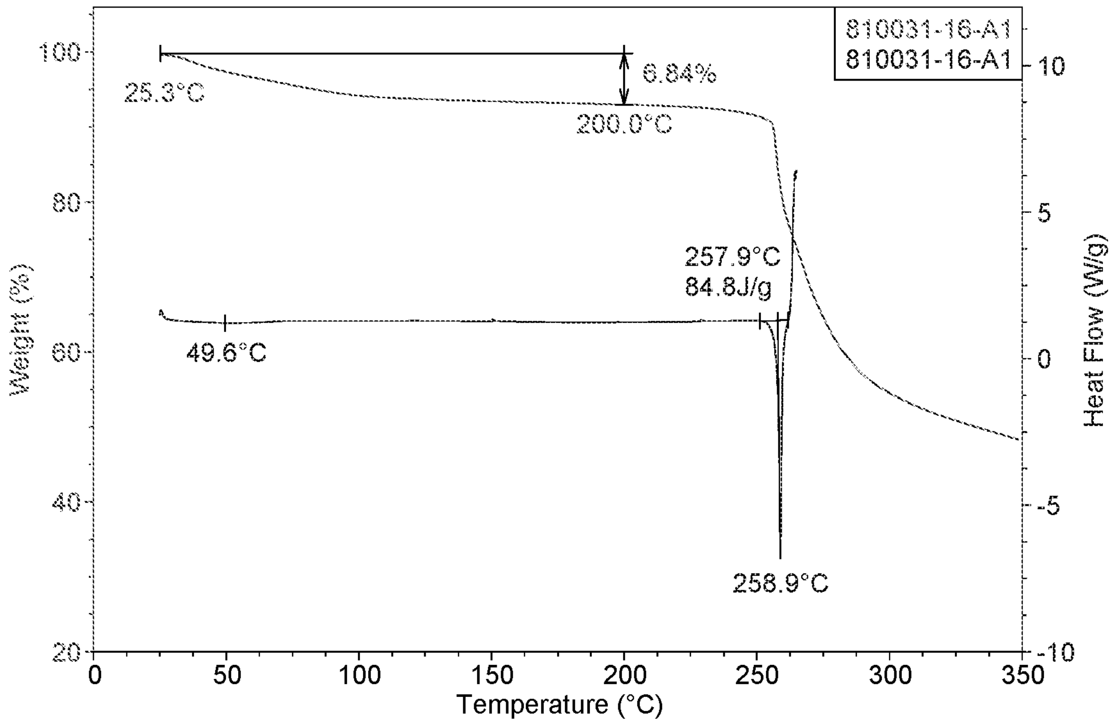
FIG. 6B shows experimental TGA and DSC data for crystalline form C of Compound 100.

Powder X-ray diffraction pattern and XRPD peaks with relative intensities of the crystalline form thus prepared are shown in FIG. 6A and Table 6, respectively. DSC and TGA data are shown in FIG. 6B.

TABLE 6

XRPD Peak Listing of Compound 100 Crystalline Form C

| °2-Theta | Relative Peak Height (%) |
|---|---|
| 4.42 | 100.0% |
| 8.83 | 50.3% |
| 10.52 | 16.5% |
| 13.27 | 53.6% |
| 16.58 | 16.8% |
| 16.97 | 24.5% |
| 17.72 | 49.6% |
| 21.18 | 7.6% |
| 22.21 | 24.9% |
| 24.49 | 14.1% |

Example 7. Use of Crystalline Form C to Prepare Crystalline Form E

Wet crystalline form C (e.g., the wet cake prior to drying from either of the above-described form C preparations) was converted to crystalline form E after 24 hours of magnetic stirring (using a magnetic stir bar) without any seeding. Similarly, wet crystalline form C, which was seeded with 1% crystalline form E, was mostly converted to form E by mechanical stirring (using a shaker) for 24-72 hours. However, even after 3 days of stirring, 5% of the material remained type C by XRPD analysis. Magnetic stirring appeared to cause a better conversion of form C to form E as compared to mechanical stirring. Without being bound by theory, we believe that magnetic stirring affects the morphology of the material and therefore make more efficient the conversion of form C to form E. It is therefore possible that grinding form C to smaller sized crystals prior to stirring could enhance the conversion of form C to form E.

The foregoing description of the present invention provides illustration and description, but is not intended to be exhaustive or to limit the invention to the precise one disclosed. Modifications and variations are possible in light of the above teachings or may be acquired from practice of the invention. Thus, the scope of the invention is defined by the claims and their equivalents.

What is claimed is:

1. A crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one selected from the group consisting of:

a. form A, characterized by an X-ray powder diffraction pattern comprising peaks at 2Θ angles of 4.43±0.2°, 11.69±0.2°, 17.75±0.2° and 27.58±0.2° and characterized by a differential scanning calorimetry pattern comprising an onset at 237° C.±2° C.;

b. form E, characterized by an X-ray powder diffraction pattern comprising peaks at 2Θ angles of 11.71±0.2°, 15.24±0.2°, 18.30±0.2°, 24.79±0.2°, and 26.15±0.2°;

c. form G, characterized by an X-ray powder diffraction pattern comprising peaks at 2Θ angles of 15.34±0.2°, 24.58±0.2°, 25.33±0.2°, and 25.86±0.2°;

d. form H, characterized by an X-ray powder diffraction pattern comprising peaks at 2Θ angles of 13.79±0.2°, 23.61±0.2°, 27.10±0.2°, and 27.49±0.2°;

e. form B, characterized by an X-ray powder diffraction pattern comprising peaks at 2Θ angles of 4.40±0.2°, 17.48±0.2°, 17.72±0.2°, 18.46±0.2°, and 27.49±0.2°; and f. form C, characterized by an X-ray powder diffraction pattern comprising peaks at 2Θ angles of 4.42±0.2°, 8.83±0.2°, 13.27±0.2°, and 17.72±0.2°.

2. The crystalline form of claim 1, wherein the crystalline form is form E, and wherein the crystalline form is further characterized by a differential scanning calorimetry pattern comprising onsets at 78.5° C.±2° C. and 256.7° C.±2° C.

3. The crystalline form of claim 1, wherein the crystalline form is form G, and wherein the crystalline form is further characterized by a differential scanning calorimetry pattern comprising onsets at 80.5° C.±2° C. and 257.2° C.±2° C.

4. A pharmaceutical composition comprising the crystalline form of claim 1, wherein the crystalline form is form A, form H, form E, or form G; and a pharmaceutically acceptable carrier.

5. A method of inhibiting one or more of TRPC1, TRPC4, and TRPC5 ion channels, or ion channels comprising a tetrameric combination of any of TRPC1, TRPC4, and TRPC5, in a subject in need of thereof, comprising administering to the subject an effective amount of a pharmaceutical composition of claim 4.

6. A method of treating a kidney disease or a nephropathy associated with a disease or condition, comprising administering to a subject in need thereof a pharmaceutical composition of claim 4.

7. A method of treating pain, anxiety, or depression, comprising administering to a subject in need thereof a pharmaceutical composition of claim 4.

8. A method of preparing the crystalline form of claim 1, wherein the crystalline form is form A, comprising the steps of:

a. dissolving an amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in an amount of a 2:1 (v/v) ratio of DMSO:ethanol at room temperature to form a supersaturated solution;

b. adding to the solution in step a. an amount of a 1:1 (v/v) ratio of ethanol:$H_2O$ sufficient to precipitate the 4-chloro-5-(4-(4-fluoro-2-(trifluoromethyl)phenoxy)-5,8-dihydropyrido [3,4-d]pyrimidin-7 (6H)-yl) pyridazin-3 (2H)-one; and c. isolating the precipitated material from step b. to produce the crystalline form A; or:

d. dissolving an amount of 4-chloro-5-(4-(4-fluoro-2-(trifluoromethyl)phenoxy)-5,8-dihydropyrido[3,4-d]pyrimidin-7(6H)-yl)pyridazin-3(2H)-one in an amount of a 2:1 (v/v) ratio of DMSO:ethanol at room temperature to form a supersaturated solution;

e. adding to the solution in step a. an amount of a 1:1 (v/v) ratio of ethanol: $H_2O$ and crystal form A seeds to precipitate the 4-chloro-5-(4-(4-fluoro-2-(trifluoromethyl)phenoxy)-5,8-dihydropyrido [3,4-d]pyrimidin-7(6H)-yl)pyridazin-3(2H)-one; and f. isolating the precipitated material from step b. to produce the crystalline form A.

9. A method of preparing a pharmaceutical composition, the method comprising providing a sample of a crystalline form of 4-chloro-5-(4-(4-fluoro-2-(trifluoromethyl)phenoxy)-5,8-dihydropyrido[3,4-d]pyrimidin-7(6H)-yl) pyridazin-3(2H)-one according to claim 1, wherein the crystalline form is form A, form H, form E, or form G, and combining the sample with a pharmaceutically acceptable excipient to produce the pharmaceutical composition.

10. A method of preparing a pharmaceutical composition, the method comprising the steps of:

a. dissolving a crystalline form of 4-chloro-5-(4-(4-fluoro-2-(trifluoromethyl)phenoxy)-5,8-dihydropyrido [3,4-d]pyrimidin-7(6H)-yl)pyridazin-3(2H)-one according to claim 1, wherein the crystalline form is form A, form H, form E, or form G, in a solvent to form a solution; and b. preparing the pharmaceutical composition from the solution.

11. A method of preparing the crystalline form of claim 1, wherein the crystalline form is form H, comprising the steps of:

a. suspending 4-chloro-5-(4-(4-fluoro-2-(trifluoromethyl) phenoxy)-5,8-dihydropyrido[3,4-d]pyrimidin-7(6H)-yl)pyridazin-3(2H)-one in a 1:1 (v/v) ratio of isopropyl alcohol: isopropyl acetate;

b. heating the suspension of step a. to a temperature of between 45° C.-55° C. for at least 24 hours with stirring; and c. isolating the insoluble material from step b. to produce the crystalline form H; or:

d. dissolving 4-chloro-5-(4-(4-fluoro-2-(trifluoromethyl) phenoxy)-5,8-dihydropyrido[3,4-dipyrimidin-7(6H)-yl)pyridazin-3(2H)-one in a 2:1 (v/v) ratio of DMSO: isopropyl alcohol at a temperature of between 45° C.-55° C.;

e. filtering the solution from step d. through a 0.45 micron PTFE membrane;

f. adding to the filtrate from step e. (i) an amount of isopropyl alcohol that is 30-50% of the amount of isopropyl alcohol used in step a.; and (ii) crystalline form H and stirring at a temperature of between 45° C.-55° C. for at least 5 minutes;

g. adding to the solution from step f. a 1:1 (v/v) ratio of isopropyl alcohol:H2O over a period of at least 4 hours with stirring while maintaining a temperature of between 45° C.-55° C. to produce a suspension of 4-chloro-5-(4-(4-fluoro-2-(trifluoromethyl)phenoxy)-5,8-dihydropyrido[3,4-d]pyrimidin-7(6H)-yl) pyridazin-3(2H)-one, wherein the amount of isopropyl alcohol added in steps f. and g. is about equal to the amount of isopropyl alcohol added in step d.;

h. maintaining the suspension from step g. at a temperature of between 45° C.-55° C. without stirring for at least 2 hours; and i. isolating the precipitated material from step h. to produce the crystalline form H; or:

j. dissolving 4-chloro-5-(4-(4-fluoro-2-(trifluoromethyl) phenoxy)-5,8-dihydropyrido[3,4-d]pyrimidin-7(6H)-yl)pyridazin-3(2H)-one in DMSO at a temperature of between 65° C.-75° C.;

k. filtering the solution from step j. through a 0.45 micron PTFE membrane;

l. adding to the filtrate from step k. (i) an amount of a 1:1 (v/v) ratio of isopropyl alcohol:$H_2O$ that is about 10% of the volume of DMSO used in step A; and (ii) crystalline form H;

m. adding to the filtrate from step 1. an additional amount of a 1:1 (v/v) ratio of isopropyl alcohol:$H_2O$ over a period of at least 5 hours with stirring while maintaining a temperature of between 65° C.-75° C., to produce a suspension of 4-chloro-5-(4-(4-fluoro-2-(trifluoromethyl)phenoxy)-5,8-dihydropyrido[3,4-d]pyrimidin-7(6H)-yl)pyridazin-3(2H)-one, wherein the total amount of isopropyl alcohol added in steps 1, and m. is about half the volume of DMSO used in step j.;

n. cooling the suspension of step m. to room temperature with stirring for at least 2 hours;

o. maintaining the suspension of step n. at room temperature without stirring for at least an additional 45 minutes; and p. isolating the precipitated material from step o. to produce the crystalline form H.

12. A method of forming the crystalline form of claim 1, wherein the crystalline form is form E, comprising the steps of:

a. suspending 4-chloro-5-(4-(4-fluoro-2-(trifluoromethyl) phenoxy)-5,8-dihydropyrido[3,4-d]pyrimidin-7(6H)-yl)pyridazin-3(2H)-one in DMF/H2O (1:9, v/v) at room temperature to form a slurry; and b. vacuum drying the suspension.

13. A method of forming the crystalline form of claim 1, wherein the crystalline form is form G, comprising the steps of:

a. suspending 4-chloro-5-(4-(4-fluoro-2-(trifluoromethyl) phenoxy)-5,8-dihydropyrido[3,4-d]pyrimidin-7(6H)-yl)pyridazin-3(2H)-one in a solvent having a $a_W$ of greater than or equal to 0.8 at room temperature to form a slurry; and b. vacuum drying the suspension.

14. A method of inhibiting a heterotetrameric form comprising a combination of (a) one or more TRPC1 ion channels with one or more TRPC4 and/or TRPC5 ion channels, or (b) one or more TRPC4 ion channels and one or more TRPC5 ion channels, in a subject in need thereof, the method comprising administering to the subject an effective amount of a pharmaceutical composition of claim 4.

15. The method of claim 14, wherein the subject is suffering from a kidney disease, pain, anxiety, or depression.

16. A crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one, which is form A, characterized by an X-ray powder diffraction pattern comprising peaks at 2Θ angles of 4.43±0.2°, 11.69±0.2°, 17.75±0.2° and 27.58±0.2° and characterized by a differential scanning calorimetry pattern comprising an onset at 237 °C±2°C.

17. The crystalline form A of claim 16, wherein the characteristic X-ray powder diffraction peaks at 2Θ angles of 4.43±0.2°, 11.69±0.2°, 17.75±0.2° and 27.58±0.2° are the highest peaks observed.

18. The crystalline form A of claim 16, characterized by an X-ray powder diffraction pattern comprising peaks at 2Θ angles of 4.43±0.2°, 11.69±0.2°, 17.75±0.2°, 22.71±0.2°, and 27.58±0.2°.

19. The crystalline form A of claim 16, characterized by an X-ray powder diffraction pattern comprising peaks at 2Θ angles of 4.43±0.2°, 11.69±0.2°, 14.24±0.2°, 16.93±0.2°, 17.75±0.2°, 22.71±0.2°, 27.58±0.2°, and 27.95±0.2°.

20. The crystalline form A of claim 16, characterized by an X-ray powder diffraction pattern comprising peaks at 2Θ angles of 4.43±0.2°, 8.80±0.2°, 9.17±0.2°, 11.69±0.2°, 12.27±0.2°, 13.28±0.2°, 14.24±0.2°, 14.67±0.2°, 15.96±0.2°, 16.93±0.2°, 17.75±0.2°, 19.64±0.2°, 20.98±0.2°, 22.23±0.2°, 22.71±0.2°, 24.19±0.2°, 25.55±0.2°, 27.58±0.2°, 27.95±0.2°, and 30.32±0.2°.

21. The crystalline form A of claim 16, characterized by an X-ray powder diffraction pattern substantially similar to FIG. 1A.

22. The crystalline form A of claim 16, characterized by a differential scanning calorimetry pattern comprising onsets at 236.4±1° C., 243.5±1° C., and 256.3° C.±1° C.

23. The crystalline form A of claim 16, characterized by a differential scanning calorimetry pattern comprising onsets at 237° C.±2° C. and 256° C.±2° C.

24. A crystalline form of 4-chloro-5-(4-(4-fluoro-2-(trifluoromethyl)phenoxy)-5,8-dihydropyrido[3,4-d]pyrimidin-7(6H)-yl)pyridazin-3(2H)-one, which is form H, characterized by an X-ray powder diffraction pattern comprising peaks at 2Θ angles of 13.79±0.2°, 23.61±0.2°,27.10±0.2°, and 27.49±0.2°.

25. The crystalline form H of claim 24, characterized by an X-ray powder diffraction pattern comprising peaks at 2Θ angles of 13.79±0.2°, 15.89±0.2°, 18.08±0.2°, 20.77±0.2°, 23.61±0.2°, 24.47±0.2°, 27.10±0.2°, and 27.49±0.2°.

26. The crystalline form H of claim 24, characterized by an X-ray powder diffraction pattern comprising peaks at 2Θ angles of 4.59±0.2°, 11.92±0.2°, 12.27±0.2°, 13.47±0.2°, 13.79±0.2°, 14.82±0.2°, 15.27±0.2°, 15.89±0.2°, 16.28±0.2°, 18.08±0.2°, 19.24±0.2°,20.77±0.2°, 23.61±0.2°, 24.47±0.2°, 25.11±0.2°, 26.13±0.2°, 27.10±0.2°, 27.49±0.2°,28.42±0.2°, and 30.49±0.2°.

27. The crystalline form H of claim 24, characterized by an X-ray powder diffraction pattern substantially similar to FIG. 2A.

28. The crystalline form H of claim 24, further characterized by a differential scanning calorimetry pattern comprising an onset at 258°±2° C.

29. The crystalline form H of claim 24, further characterized by a differential scanning calorimetry pattern comprising onsets at 74.1° C.±1° C. and 241.4° C.±1° C.

30. The crystalline form H of claim 24, wherein the characteristic X-ray powder diffraction peaks at 2Θ angles of 13.79±0.2°, 23.61±0.2°, 27.10±0.2°, and 27.49±0.2 are the highest peaks observed.

31. The crystalline form of claim 1, wherein the crystalline form is Form E.

32. The crystalline form of claim 1, wherein the crystalline form is Form G.

33. The crystalline form of claim 1, wherein the crystalline form is Form B.

34. The crystalline form of claim 1, wherein the crystalline form is Form C.

* * * * *